(12) United States Patent
St. Germain et al.

(10) Patent No.: US 10,226,324 B2
(45) Date of Patent: Mar. 12, 2019

(54) DEVICES AND METHODS FOR GASTROINTESTINAL BYPASS

(71) Applicant: ValenTx, Inc., Maple Grove, MN (US)

(72) Inventors: Jon St. Germain, Elk River, MN (US);
Cole Chen, Maple Grove, MN (US);
Roland Maude-Griffin, Edina, MN (US); Johann Neisz, Coon Rapids, MN (US); Sean Miller, Plymouth, MN (US)

(73) Assignee: ValenTx, Inc., Maple Grove, MN (US)

( * ) Notice: Subject to any disclaimer, the term of this patent is extended or adjusted under 35 U.S.C. 154(b) by 559 days.

(21) Appl. No.: 14/930,655

(22) Filed: Nov. 2, 2015

(65) Prior Publication Data
US 2016/0193065 A1 Jul. 7, 2016

Related U.S. Application Data

(60) Provisional application No. 62/073,927, filed on Oct. 31, 2014, provisional application No. 62/147,588, filed on Apr. 15, 2015.

(51) Int. Cl.
| | |
|---|---|
| *A61F 5/00* | (2006.01) |
| *A61F 2/04* | (2013.01) |
| *A61B 17/04* | (2006.01) |
| *A61F 2/95* | (2013.01) |
| *A61B 17/00* | (2006.01) |

(52) U.S. Cl.
CPC .............. *A61F 2/04* (2013.01); *A61B 17/0401* (2013.01); *A61F 5/0076* (2013.01); *A61F 5/0089* (2013.01); *A61B 2017/00867* (2013.01); *A61B 2017/0409* (2013.01); *A61B 2017/0419* (2013.01); *A61B 2017/0464* (2013.01); *A61F 2/95* (2013.01); *A61F 2002/044* (2013.01);
(Continued)

(58) Field of Classification Search
CPC ........ A61F 2/04; A61F 5/0076; A61F 5/0089; A61B 17/0401; A61B 2017/0409; A61B 2017/0419
See application file for complete search history.

(56) References Cited

U.S. PATENT DOCUMENTS 4,581,026 A * 4/1986 Schneider ............... A61F 5/453
604/352
8,147,441 B2 4/2012 Gannoe et al.
(Continued)

OTHER PUBLICATIONS

PCT application PCT/US2015/058690, Mar. 17, 2016 ISR / WO.
PCT application PCT/US2015/058691, Jan. 27, 2016 ISR / WO.

*Primary Examiner* — Leslie Deak
(74) *Attorney, Agent, or Firm* — Jinn Su

(57) ABSTRACT

Delivery devices are described. In one embodiment, a delivery device includes a catheter and a sealing pad coupled to an outer surface of the catheter. The delivery device may further include a recess formed in an outer surface of the catheter. The sealing pad may be coupled in the recess.
Methods for delivering a tubular device are described. In one embodiment, a method may include inserting a distal end of a catheter into a lumen of a tubular device. The catheter may include a sealing pad coupled to an outer surface of the catheter. The method also includes positioning the sealing pad inside a drawstring coupled circumferentially to the tubular device, and cinching the drawstring around the catheter at the sealing pad to couple the tubular device to the catheter.

13 Claims, 32 Drawing Sheets

(52) U.S. Cl.
CPC . *A61F 2002/045* (2013.01); *A61F 2230/0069* (2013.01); *A61F 2250/0063* (2013.01)

(56) References Cited

U.S. PATENT DOCUMENTS

| | | |
|---|---|---|
| 8,956,318 B2 | 2/2015 | Miller et al. |
| 2006/0212052 A1 | 9/2006 | Shin et al. |
| 2009/0012541 A1 | 1/2009 | Dahl et al. |
| 2010/0121462 A1 | 5/2010 | Sobrino-Serrano et al. |
| 2012/0095384 A1 | 4/2012 | Babkes et al. |
| 2012/0184893 A1 | 7/2012 | Thompson et al. |
| 2013/0324905 A1 | 12/2013 | Nelson et al. |
| 2013/0324926 A1* | 12/2013 | Nelson ............... A61F 2/04 604/115 |
| 2014/0180192 A1 | 6/2014 | Ortiz et al. |
| 2014/0188245 A1 | 7/2014 | Neisz et al. |
| 2016/0193063 A1 | 7/2016 | St. Germain et al. |

\* cited by examiner

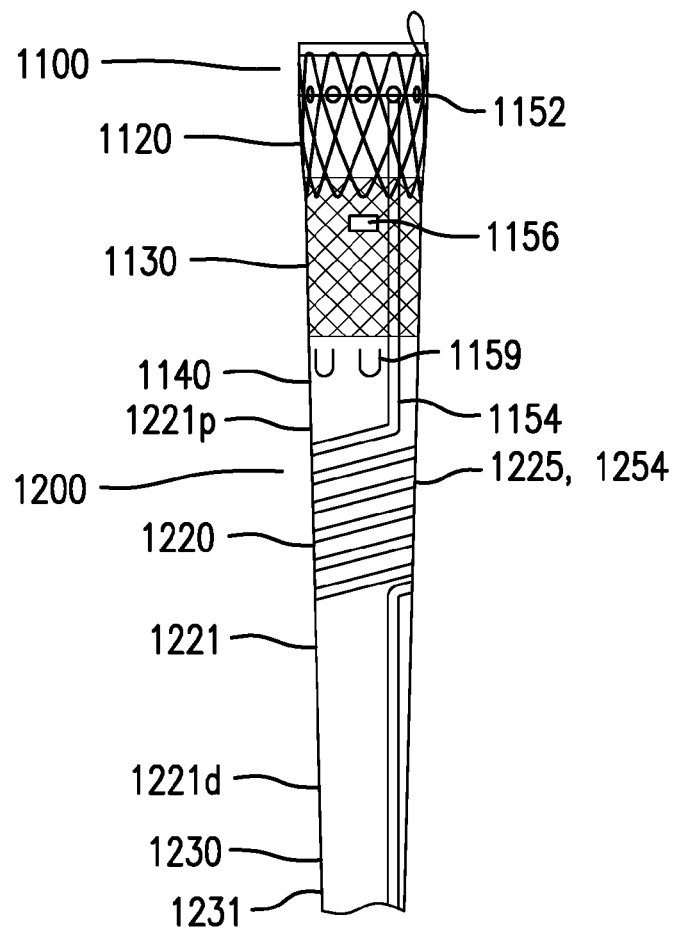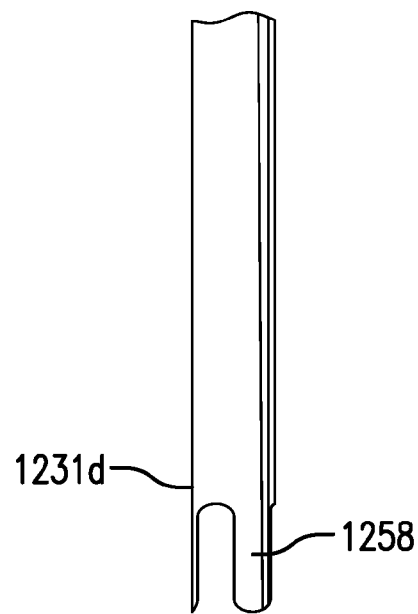
FIG.1A

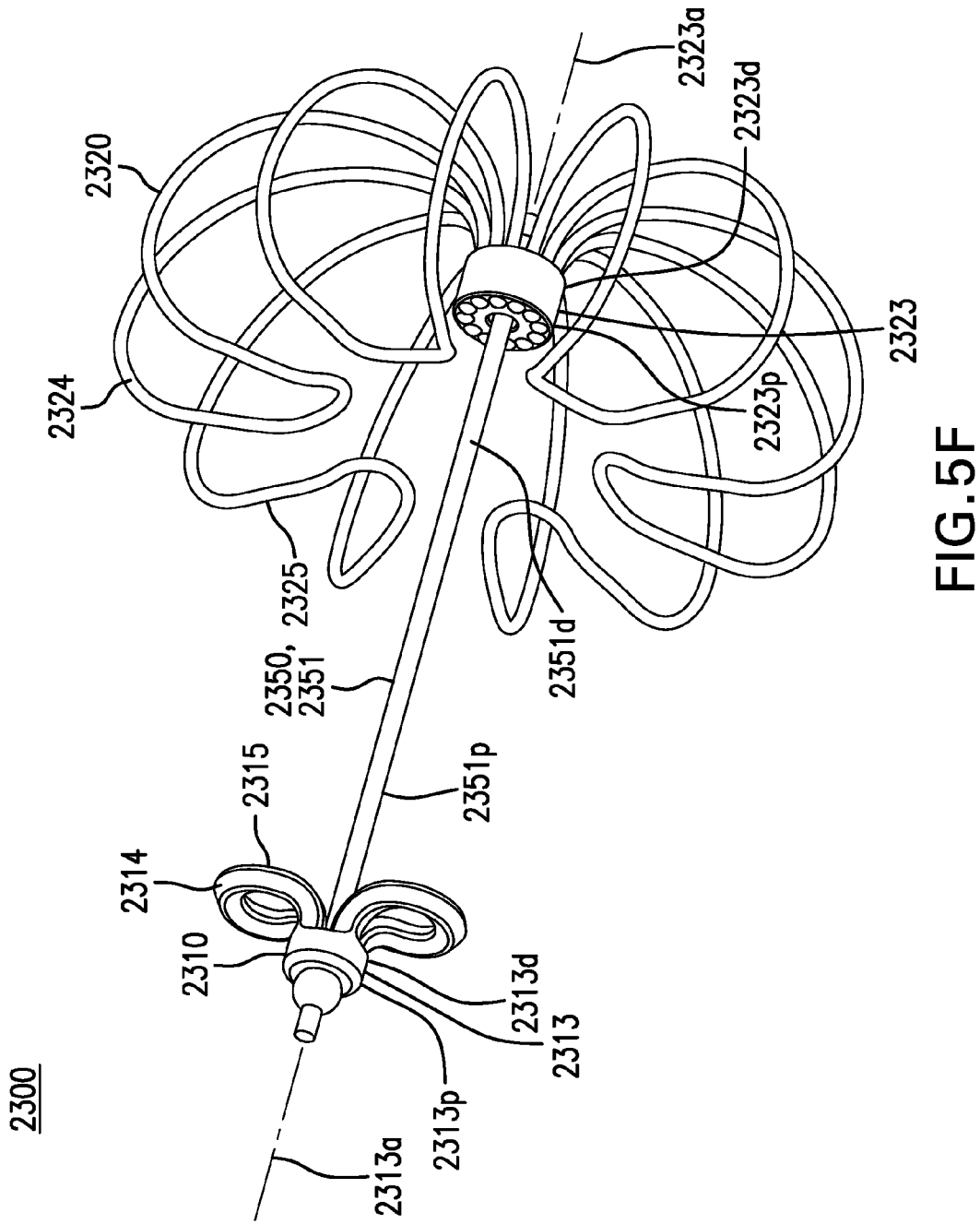

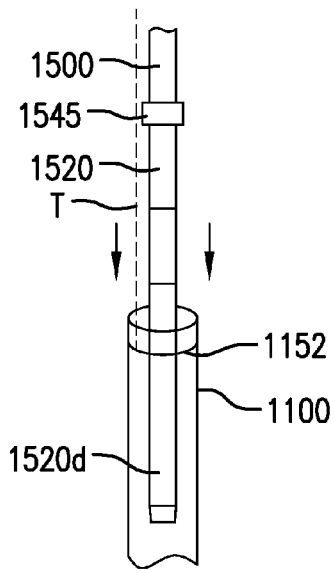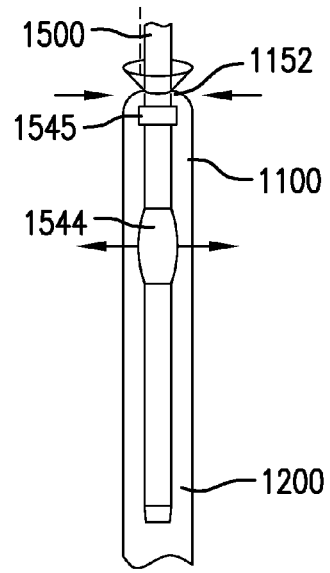
FIG.10A  FIG.10B
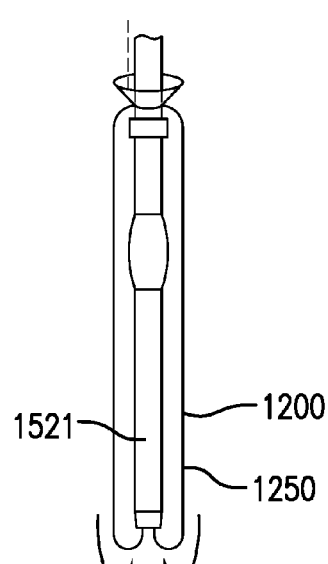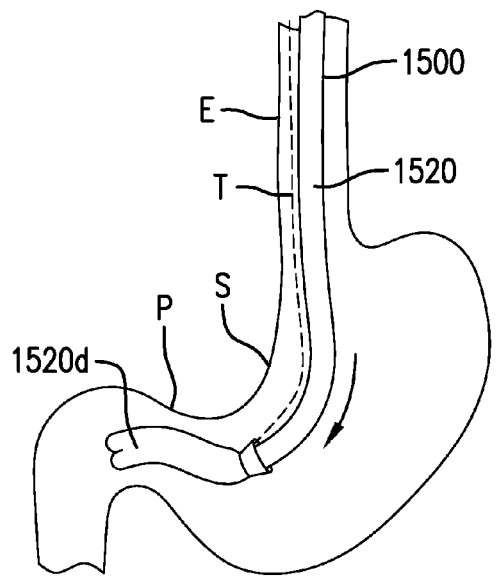
FIG.10C  FIG.10D

DEVICES AND METHODS FOR GASTROINTESTINAL BYPASS

CROSS-REFERENCE TO RELATED APPLICATIONS

This application claims the benefit of U.S. provisional application Nos. 62/073,927, filed Oct. 31, 2014, and 62/147,588, filed Apr. 15, 2015. These applications are hereby incorporated by reference in their entireties.

BACKGROUND

Diabetes, heart disease, and other obesity-related conditions may be treated surgically with bariatric procedures such as jejuno-ileal bypass, jejuno-colic bypass, biliopancreatic diversion, gastric bypass, vertical sleeve gastrectomy, adjustable gastric banding, and gastroplasty. These procedures may be effective for weight control and treatment of chronic conditions. However, these procedures carry with them substantial shortcomings, including the risk of infection and other risks accompanying surgery. Some of these procedures induce radical permanent changes to the gastrointestinal anatomy, thus foreclosing subsequent surgical intervention.

What is needed are devices and methods that use non-surgical techniques that avoid the risks associated with gastrointestinal bypass surgery. What is also needed are devices and methods for gastrointestinal bypass that allow for additional or revision procedures to be performed. What is also needed are devices and methods for gastrointestinal bypass that are reversible.

SUMMARY

Delivery devices are described. In one embodiment, a delivery device includes a catheter and a sealing pad coupled to an outer surface of the catheter. The delivery device may further include a recess formed in an outer surface of the catheter. The sealing pad may be coupled in the recess.

Methods for delivering a tubular device are described. In one embodiment, a method may include inserting a distal end of a catheter into a lumen of a tubular device. The catheter may include a sealing pad coupled to an outer surface of the catheter. The method also includes positioning the sealing pad inside a drawstring coupled circumferentially to the tubular device, and cinching the drawstring around the catheter at the sealing pad to couple the tubular device to the catheter.

Methods for attaching a device to a tissue wall are described. In one embodiment, the method includes applying a vacuum to an anchoring cavity of a catheter to draw an anchoring membrane of the device and the tissue wall into the anchoring cavity to form a bulge. The method also includes advancing a delivery needle out of a secondary lumen of the catheter through the bulge from a first side of the anchoring membrane and a first side of the tissue wall to position a tip of the delivery needle on a second side of the tissue wall. The method also includes pushing a second retention element of a tissue anchor out of a lumen of the delivery needle on the second side of the tissue wall. The method also includes pulling the delivery needle back through the bulge to place a tension element of the tissue anchor through the anchoring membrane and the tissue wall. The tension element may be coupled to the second retention element.

BRIEF DESCRIPTION OF THE DRAWINGS

FIGS. 1A-1B show one embodiment of a gastrointestinal bypass device 1000.

FIGS. 5D-5G show other embodiments of a tissue anchor 2300.

FIGS. 5H-5I show other embodiments of a tissue anchor 3300.

DESCRIPTION

Figure 1B:
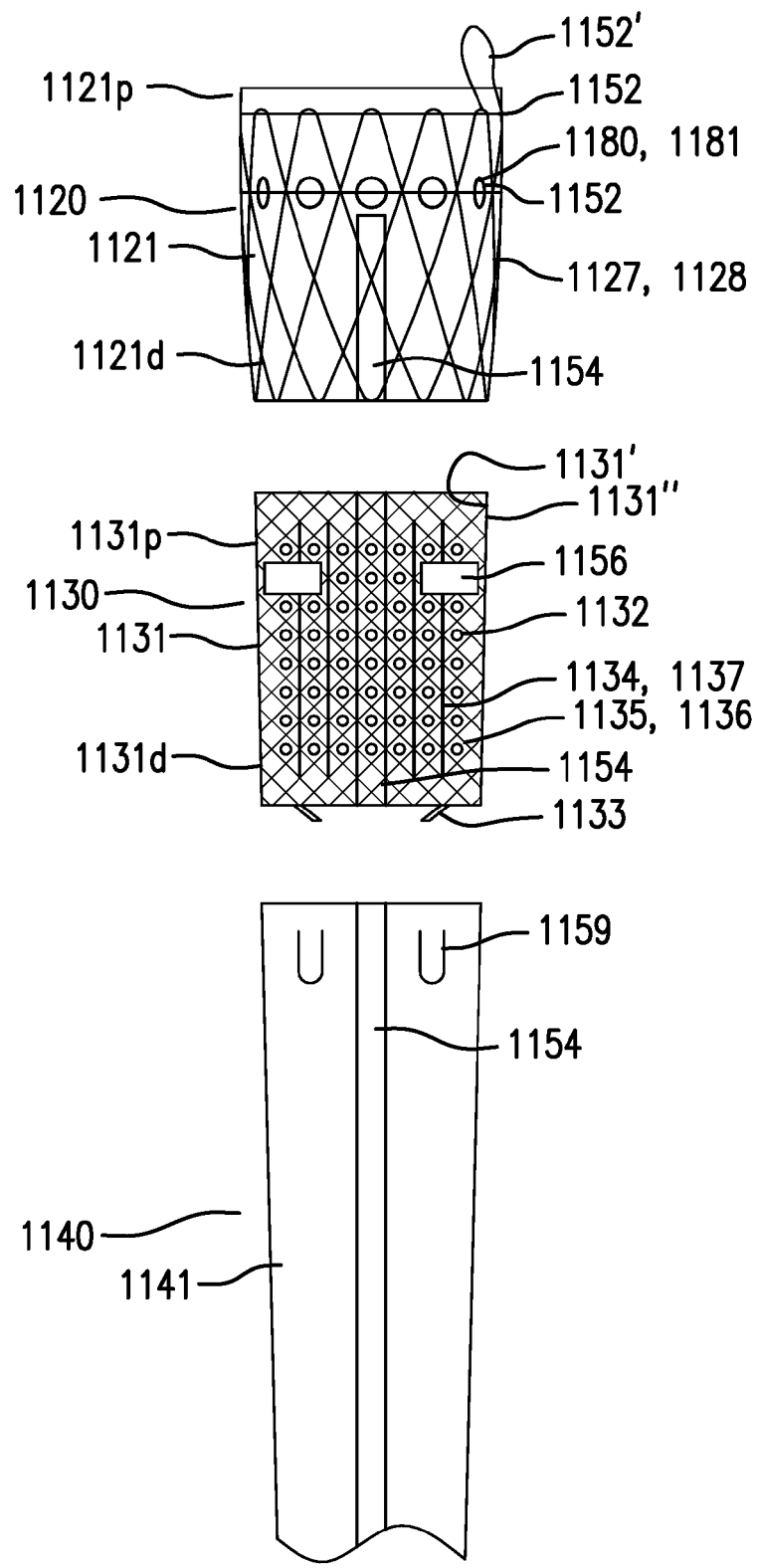

FIGS. 1A-1B show one embodiment of a gastrointestinal bypass device 1000. FIG. 1A shows a side view of gastrointestinal bypass device 1000. FIG. 1B shows an exploded view of cuff 1100 of gastrointestinal bypass device 1000.

Gastrointestinal bypass device 1000 may be configured to receive swallowed food in the esophagus and bypass the food into the intestine.

Gastrointestinal bypass device 1000 may include a cuff 1100.

Cuff 1100 may include a capture portion 1120.

Capture portion 1120 may include a capture liner 1121. Capture liner 1121 may include a proximal portion 1121p and a distal portion 1121d.

Capture liner 1121 may be configured to be placed in the esophagus. Capture liner 1121 may be configured to capture or receive swallowed food in the esophagus so that the food may be bypassed into the intestine. Capture liner 1121 may be configured to conform to the inside of the esophagus to reduce the amount of food that is not captured and bypassed. Capture liner 1121 may have an outward bias configured to conform to the inside of the esophagus. Capture liner 1121 may have an outward bias that is not sufficient to retain cuff 1100 in the esophagus.

Capture liner 1121 may be funnel-shaped, with proximal portion 1121p having a width greater than distal portion 1121d. Alternatively, capture liner 1121 may have a width that is constant.

Capture liner 1121 may be configured to reduce its impact on the ability of the esophagus to open and close. Capture liner 1121 may be flexible.

Capture liner 1121 may include one or more layers. Capture liner 1121 may be at least semi-permeable to food and/or liquids. Capture liner 1121 may be made of silicone, polyethylene, polypropylene, a polyurethane such as PELLETHANE, DACRON, a woven material, a mesh material, or other suitable material.

Capture portion 1120 may include a conformance structure 1127. Conformance structure 1127 may be coupled to capture liner 1121.

Conformance structure 1127 may be configured to enhance conformance of capture liner 1121 to the inside of the esophagus. Conformance structure 1127 may have an outward bias configured to enhance conformance of capture liner 1121 to the inside of the esophagus. Conformance structure 1127 may have an outward bias that is not sufficient to retain capture cuff 1100 in the esophagus.

Conformance structure 1127 may include a stent 1128. Stent 1128 may be made of metal, plastic, or other suitable material. Conformance structure 1127 may include a mesh, a braid, or other suitable structure.

Conformance structure 1127 may be coupled between two layers of capture liner 1121. Conformance structure 1127 may be coupled between two layers of capture liner 1121 blow molded to sandwich conformance structure 1127. Conformance structure 1127 may provide a substrate on which at least a portion of capture liner 1121 is formed, such as by dip coating, spray coating, or other suitable methods.

Cuff 1100 includes an anchoring portion 1130.

Anchoring portion 1130 may include an anchoring membrane 1131. Anchoring membrane 1131 may include a proximal portion 1131p, a distal portion 1131d, a first side 1131', and a second side 1131". Anchoring membrane 1131 may be coupled to distal portion 1121d of capture liner 1121. Alternatively, anchoring membrane 1131 may be coupled to proximal portion 1121p of capture liner 1121.

Anchoring membrane 1131 may be configured to be placed in the esophagus. Anchoring membrane 1131 may be configured to be placed next to a wall of the esophagus. Anchoring membrane 1131 may be configured to be attached to a tissue anchor. Anchoring membrane 1131 may be configured to be attached to the wall of the esophagus with a tissue anchor placed through anchoring membrane 1131. Anchoring membrane 1131 may be configured to be pierced to allow a tissue anchor to be placed through anchoring membrane 1131 and attach anchoring membrane 1131 to the wall of the esophagus. Anchoring membrane 1131 may be configured to retain a tissue anchor placed through anchoring membrane 1131. Anchoring membrane 1131 may be sufficiently strong to prevent a tissue anchor placed through anchoring membrane from pulling through and/or tearing anchoring membrane 1131.

Anchoring membrane 1131 may be configured to be collapsible. Anchoring membrane 1131 may be configured to be pulled or collapsed with a vacuum applied to first side 1131' of anchoring membrane 1131. Anchoring membrane 1131 may be configured to be pulled or collapsed with a grasper or hook from first side 1131' of anchoring membrane 1131. Anchoring membrane 1131 may be configured to be pulled or collapsed toward first side 1131' of anchoring membrane 1131.

Anchoring membrane 1131 may be configured to reduce its impact on the ability of the esophagus to open and close. Anchoring membrane 1131 may be flexible. Anchoring membrane 1131 may be stretchable and recover without permanent set.

Anchoring membrane 1131 may include one or more layers. Anchoring membrane 1131 may be at least semi-permeable to food and/or liquids. Anchoring membrane 1131 may be made of silicone, polyethylene, polypropylene, a polyurethane such as PELLETHANE, DACRON, a woven material, a mesh material, or other suitable material.

Anchoring membrane 1131 may include one or more perforations 1132 formed in anchoring membrane 1131.

Perforations 1132 may be configured to allow at least a portion of a vacuum applied to one side of anchoring membrane 1131 to reach through anchoring membrane 1131. Perforations 1132 may be configured to allow at least a portion of a vacuum applied to anchoring membrane 1131 to reach a tissue wall placed next to anchoring membrane 1131. Perforations 1132 may be configured to allow at least a portion of a vacuum applied to first side 1131' of anchoring membrane 1131 to reach a tissue wall placed next to second side 1131" of anchoring membrane 1131.

Perforations 1132 may include any one or any combination of holes, slits, and other openings of any suitable shape and size.

Anchoring membrane 1131 may include one or more pulls 1133. Pulls 1133 may be coupled to anchoring membrane 1131 and/or reinforcement structure 1135. Pulls 1133 may extend from first side 1131' of anchoring membrane 1131.

Pulls 1133 may be configured to allow anchoring membrane 1131 to be pulled or collapsed. Pulls 1133 may be configured to allow anchoring membrane 1131 to be pulled or collapsed toward first side 1131' of anchoring membrane 1131.

Pulls 1133 may include any one or any combination of loops, tabs, and other suitable structures. Pulls 1133 may be made of a biodegradable material.

Anchoring membrane 1131 may include one or more creases 1134. Creases 1134 may be formed by scoring anchoring membrane 1131 and/or forming thinner portions of anchoring membrane 1131. Creases 1134 may be configured to allow anchoring membrane 1131 to collapse along creases 1134. Creases 1134 may allow anchoring membrane 1131 to be more easily and/or predictably pulled or collapsed.

Anchoring portion 1130 may include a reinforcement structure 1135. Reinforcement structure 1135 may be coupled to anchoring membrane 1131.

Reinforcement structure 1135 may be configured to reinforce anchoring membrane 1131. Reinforcement structure 1135 may be configured to retain a tissue anchor placed through reinforcement structure 1135. Reinforcement structure 1135 may be configured to reduce the likelihood of a tissue anchor placed through anchoring membrane 1131 pulling through and/or tearing anchoring membrane 1131.

Reinforcement structure 1135 may include a braid 1136. Braid 1136 may have uniform or varying opening sizes. Braid 1136 may be made of plastic, metal, or other suitable material. Reinforcement structure 1135 may include a stent, mesh, or other suitable structure.

Reinforcement structure 1135 may be coupled between two layers of anchoring membrane 1131. Reinforcement structure 1135 may be coupled between two layers of anchoring membrane 1131 blow molded to sandwich reinforcement structure 1135. Reinforcement structure 1135 may provide a substrate on which at least a portion of anchoring membrane 1131 is formed, such as by dip coating, spray coating, or other suitable methods.

Reinforcement structure 1135 may include one or more creases 1137. Creases 1137 may be formed by scoring reinforcement structure 1135 and/or forming thinner portions of reinforcement structure 1135. Creases 1137 may be configured to allow reinforcement structure 1135 to collapse along creases 1137. Creases 1137 may allow reinforcement structure 1135 to be more easily and/or predictably pulled or collapsed.

Cuff 1100 may include a lower esophageal sphincter (LES) portion 1140.

LES portion 1140 may include an LES liner 1141. LES liner 1141 may be coupled to distal portion 1131*d* of anchoring membrane 1131.

LES liner 1141 may be configured to be placed through the LES. LES liner 1141 may be configured to allow the LES to close normally. LES liner 1141 may be thinner and/or more flexible than capture liner 1121 and/or anchoring membrane 1131.

LES liner 1141 may include one or more layers. LES liner 1141 may be at least semi-permeable to food and/or liquids. LES liner 1141 may be made of silicone, polyethylene, polypropylene, a polyurethane such as PELLETHANE, DACRON, a woven material, a mesh material, or other suitable material.

Capture liner 1121, anchoring membrane 1131, and LES liner 1141 may have the same or different properties. Capture liner 1121, anchoring membrane 1131, and LES liner 1141 may be made of the same or different materials and/or thicknesses.

Conformance structure 1127 and reinforcement structure 1135 may have the same or different properties. Conformance structure 1127 and reinforcement structure 1135 may be made of the same or different materials and/or thicknesses. Conformance structure 1127 may overlap with reinforcement structure 1135.

Any combination of capture liner 1121, anchoring membrane 1131, LES liner 1141, conformance structure 1127, and reinforcement structure 1135 may be formed as one or more pieces. For example, capture liner 1121 and conformance structure 1127 may be formed as a single piece.

Capture liner 1121, anchoring membrane 1131, and LES liner 1141 may have the same or different widths. Capture liner 1121 may have a width the same as or greater than anchoring membrane 1131 and/or LES liner 1141. Anchoring membrane 1131 may have a width the same as or greater than LES liner 1141. LES liner 1141 with a width smaller than capture liner 1121 and/or anchoring membrane 1131 may act as a restriction device, and may contribute to a sense of fullness. LES liner 1141 with a width smaller than capture liner 1121 and/or anchoring membrane 1131 may push capture liner 1121 and/or anchoring membrane 1131 in a proximal direction when the LES closes and help keep cuff 1100 in place.

Capture liner 1121, anchoring membrane 1131, and LES liner 1141 may each have a length of approximately 10 mm to 40 mm. Capture liner 1121, anchoring membrane 1131, and LES liner 1141 may have widths of approximately 15 mm to 35 mm. For example, capture liner 1121 may have a width of approximately 25 mm, anchoring membrane 1131 may have a width of approximately 22 mm, and LES liner 1141 may have a width of approximately 15 mm.

Cuff 1100 may include one or more drawstrings 1152. Drawstrings 1152 may be coupled to one or more of capture liner 1121, anchoring membrane 1131, and LES liner 1141. Drawstrings 1152 may be at least partially coupled around one or more of capture liner 1121, anchoring membrane 1131, and LES liner 1141. Drawstrings 1152 may be configured to reduce a width of one or more of capture liner 1121, anchoring membrane 1131, and LES liner 1141 for delivery and/or removal of cuff 1100. Drawstrings 1152 may be removable or non-removable. One or more drawstrings 1152 may include a loose portion forming a loop 1152' which may facilitate grasping drawstring 1152.

Cuff 1100 may include at least one stiffening member 1154. Stiffening member 1154 may be coupled along at least a portion of a length of cuff 1100. Stiffening member 1154 may be configured to reduce the likelihood of cuff 1100 inverting. Stiffening member 1154 may be bonded to one or more of capture liner 1121, anchoring membrane 1131, and LES liner 1141. Stiffening member 1154 may be elongate. Stiffening member 1154 be made of metal, plastic, or other suitable material. Stiffening member 1154 may be radiopaque.

Cuff 1100 may include one or more radiopaque markers 1156. Radiopaque markers 1156 may be coupled to cuff 1100. Radiopaque markers 1156 may be configured to facilitate delivery of cuff 1100.

Cuff 1100 may include one or more nonbypass features 1159. Nonbypass features 1159 may be coupled to and/or formed in one or more of capture liner 1121, anchoring membrane 1131, and LES liner 1141. Nonbypass features 1159 may be configured to allow a portion of food to pass from the inside of cuff 1100 to the outside of cuff 1100. Nonbypass features 1159 may include any one or any combination of openings, valves, flaps, and other features.

Cuff 1100 may include one or more tissue ingrowth elements 1180. Tissue ingrowth elements 1180 may be configured to allow the wall of the esophagus to grow into cuff 1100.

Figure 2A:
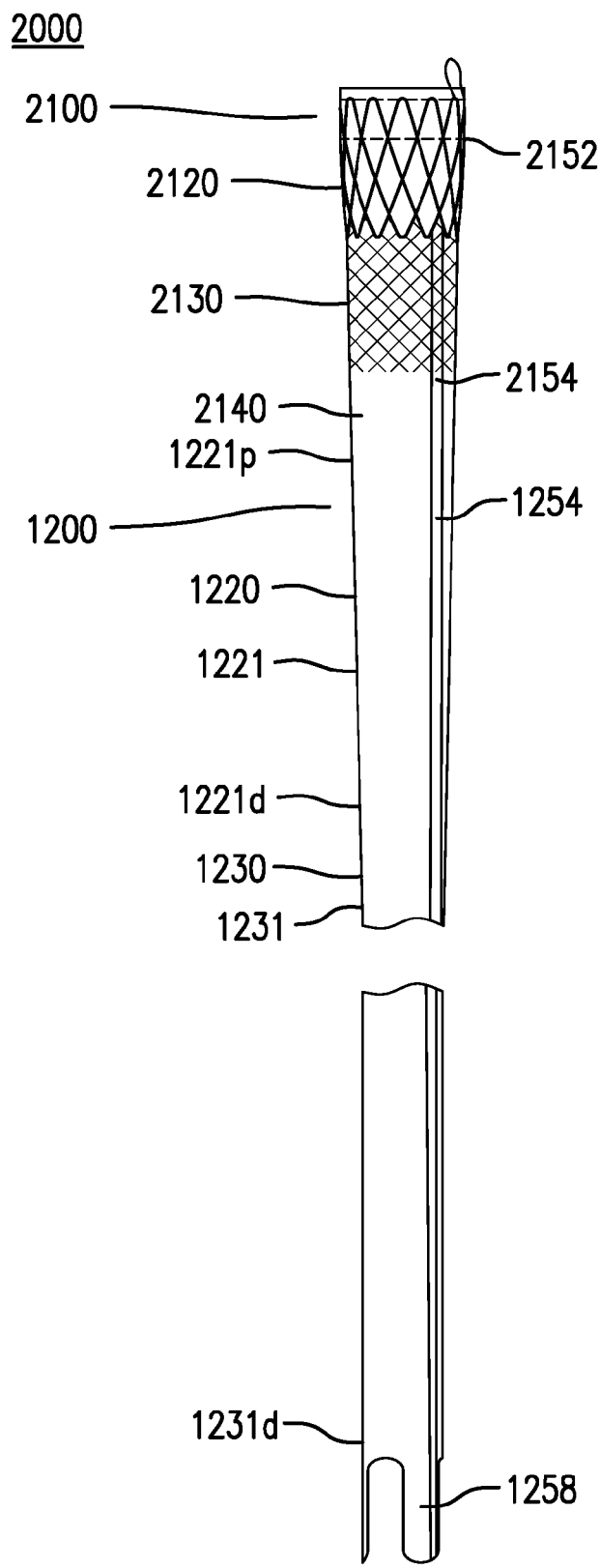
FIGS. 2A-2B show another embodiment of a gastrointestinal bypass device 2000.
Figure 2B:
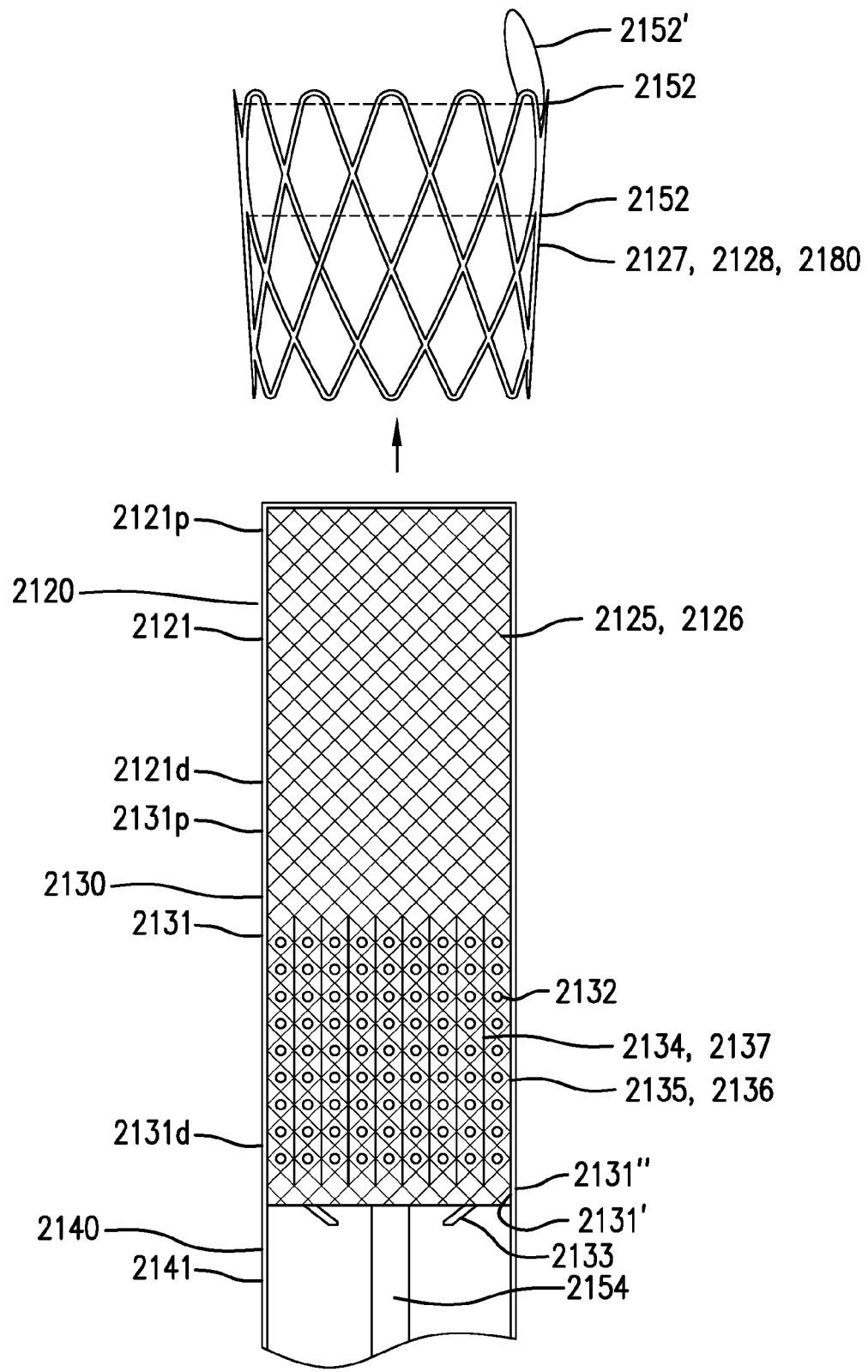

Tissue ingrowth elements 1180 may include one or more holes 1181 formed in capture liner 1121 and/or anchoring membrane 1131. Holes 1181 may be configured to allow tissue ingrowth FIGS. 2A-2B show another embodiment of a gastrointestinal bypass device 2000. FIG. 2A shows a side view of gastrointestinal bypass device 2000. FIG. 2B shows an exploded view of cuff 2100 of gastrointestinal bypass device 2000.

Gastrointestinal bypass device 2000 may be configured to receive swallowed food in the esophagus and bypass the food into the intestine.

Gastrointestinal bypass device 2000 may include a cuff 2100.

Cuff 2100 may include a capture portion 2120.

Capture portion 2120 may include a capture liner 2121. Capture liner 2121 may include a proximal portion 2121*p* and a distal portion 2121*d*.

Capture liner 2121 may be configured to be placed in the esophagus. Capture liner 2121 may be configured to capture or receive swallowed food in the esophagus so that the food may be bypassed into the intestine. Capture liner 2121 may be configured to conform to the inside of the esophagus to reduce the amount of food that is not captured and bypassed. Capture liner 2121 may have an outward bias configured to conform to the inside of the esophagus. Capture liner 2121 may have an outward bias that is not sufficient to retain cuff 2100 in the esophagus.

Capture liner 2121 may be funnel-shaped, with proximal portion 2121*p* having a width greater than distal portion 2121*d*. Alternatively, capture liner 2121 may have a width that is constant.

Capture liner 2121 may be configured to reduce its impact on the ability of the esophagus to open and close. Capture liner 2121 may be flexible.

Capture liner 2121 may include one or more layers. Capture liner 2121 may be at least semi-permeable to food and/or liquids. Capture liner 2121 may be made of silicone, polyethylene, polypropylene, a polyurethane such as PELLETHANE, DACRON, a woven material, a mesh material, or other suitable material.

Capture portion 2120 may include a conformance structure 2127. Conformance structure 2127 may be coupled to capture liner 2121.

Conformance structure 2127 may be configured to enhance conformance of capture liner 2121 to the inside of the esophagus. Conformance structure 2127 may have an outward bias configured to enhance conformance of capture liner 2121 to the inside of the esophagus. Conformance structure 2127 may have an outward bias that is not sufficient to retain capture cuff 2100 in the esophagus.

Conformance structure 2127 may include a stent 2128. Stent 2128 may be made of metal, plastic, or other suitable material. Conformance structure 2127 may include a mesh, a braid, or other suitable structure.

Conformance structure 2127 may be coupled to an outside of capture liner 2121. Conformance structure 2127 may be coupled to capture liner 2121 with sutures or other suitable method.

Capture portion 2120 may include an attachment structure 2125. Attachment structure 2125 may be coupled to capture liner 2121.

Attachment structure 2125 may be configured to facilitate coupling conformance structure 2127 to capture liner 2121. Attachment structure 2125 may provide a structure to which conformance structure 2127 may be sutured and/or otherwise coupled.

Attachment structure 2125 may include a braid 2126. Braid 2126 may be made of plastic, metal, or other suitable material. Braid 2126 may have uniform or varying opening sizes. Attachment structure 2125 may include a stent, a mesh, or other suitable structure.

Attachment structure 2125 may be coupled between two layers of capture liner 2121. Attachment structure 2125 may be coupled between two layers of capture liner 2121 blow molded to sandwich attachment structure 2125. Attachment structure 2125 may provide a substrate on which at least a portion of capture liner 2121 is formed, such as by dip coating, spray coating, or other suitable methods.

Cuff 2100 includes an anchoring portion 2130.

Anchoring portion 2130 may include an anchoring membrane 2131. Anchoring membrane 2131 may include a proximal portion 2131p and a distal portion 2131d. Anchoring membrane 2131 may be coupled to distal portion 2121d of capture liner 2121. Alternatively, anchoring membrane 2131 may be coupled to proximal portion 2121p of capture liner 2121.

Anchoring membrane 2131 may be configured to be placed in the esophagus. Anchoring membrane 2131 may be configured to be placed next to a wall of the esophagus. Anchoring membrane 2131 may be configured to be attached to a tissue anchor. Anchoring membrane 2131 may be configured to be attached to the wall of the esophagus with a tissue anchor placed through anchoring membrane 2131. Anchoring membrane 2131 may be configured to be pierced to allow a tissue anchor to be placed through anchoring membrane 2131 and attach anchoring membrane 2131 to the wall of the esophagus. Anchoring membrane 2131 may be configured to retain a tissue anchor placed through anchoring membrane 2131. Anchoring membrane 2131 may be sufficiently strong to prevent a tissue anchor placed through anchoring membrane from pulling through and/or tearing anchoring membrane 2131.

Anchoring membrane 2131 may be configured to be collapsible. Anchoring membrane 2131 may be configured to be pulled or collapsed with a vacuum applied to first side 2131' of anchoring membrane 2131. Anchoring membrane 2131 may be configured to be pulled or collapsed with a grasper or hook from first side 2131' of anchoring membrane 2131. Anchoring membrane 2131 may be configured to be pulled or collapsed toward first side 2131' of anchoring membrane 2131.

Anchoring membrane 2131 may be configured to reduce its impact on the ability of the esophagus to open and close. Anchoring membrane 2131 may be flexible. Anchoring membrane 2131 may be stretchable and recover without permanent set.

Anchoring membrane 2131 may include one or more layers. Anchoring membrane 2131 may be at least semi-permeable to food and/or liquids. Anchoring membrane 2131 may be made of silicone, polyethylene, polypropylene, a polyurethane such as PELLETHANE, DACRON, a woven material, a mesh material, or other suitable material.

Anchoring membrane 2131 may include one or more perforations 2132 formed in anchoring membrane 2131.

Perforations 2132 may be configured to allow at least a portion of a vacuum applied to one side of anchoring membrane 2131 to reach through anchoring membrane 2131. Perforations 2132 may be configured to allow at least a portion of a vacuum applied to anchoring membrane 2131 to reach a tissue wall placed next to anchoring membrane 2131. Perforations 2132 may be configured to allow at least a portion of a vacuum applied to first side 2131' of anchoring membrane 2131 to reach a tissue wall placed next to second side 2131" of anchoring membrane 2131.

Perforations 2132 may include any one or any combination of holes, slits, and other openings of any suitable shape and size.

Anchoring membrane 2131 may include one or more pulls 2133. Pulls 2133 may be coupled to anchoring membrane 2131 and/or reinforcement structure 2135. Pulls 2133 may extend from first side 2131' of anchoring membrane 2131.

Pulls 2133 may be configured to allow anchoring membrane 2131 to be pulled or collapsed. Pulls 2133 may be configured to allow anchoring membrane 2131 to be pulled or collapsed toward first side 2131' of anchoring membrane 2131.

Pulls 2133 may include any one or any combination of loops, tabs, and other suitable structures. Pulls 2133 may be made of a biodegradable material.

Anchoring membrane 2131 may include one or more creases 2134. Creases 2134 may be formed by scoring anchoring membrane 2131 and/or forming thinner portions of anchoring membrane 2131. Creases 2134 may be configured to allow anchoring membrane 2131 to collapse along creases 2134. Creases 2134 may allow anchoring membrane 2131 to be more easily and/or predictably pulled or collapsed.

Anchoring portion 2130 may include a reinforcement structure 2135. Reinforcement structure 2135 may be coupled to anchoring membrane 2131.

Reinforcement structure 2135 may be configured to reinforce anchoring membrane 2131. Reinforcement structure 2135 may be configured to retain a tissue anchor placed through reinforcement structure 2135. Reinforcement structure 2135 may be configured to reduce the likelihood of a tissue anchor placed through anchoring membrane 2131 pulling through and/or tearing anchoring membrane 2131.

Reinforcement structure 2135 may include a braid 2136. Braid 2136 may have uniform or varying opening sizes. Braid 2136 may be made of plastic, metal, or other suitable material. Reinforcement structure 2135 may include a stent, mesh, or other suitable structure.

Reinforcement structure 2135 may be coupled between two layers of anchoring membrane 2131. Reinforcement structure 2135 may be coupled between two layers of anchoring membrane 2131 blow molded to sandwich reinforcement structure 2135. Reinforcement structure 2135 may provide a substrate on which at least a portion of anchoring membrane 2131 is formed, such as by dip coating, spray coating, or other suitable methods.

Anchoring membrane 2131 may include one or more creases 2137. Creases 2137 may be formed by scoring anchoring membrane 2131 and/or forming thinner portions of anchoring membrane 2131. Creases 2137 may be configured to allow anchoring membrane 2131 to collapse along creases 2137. Creases 2137 may allow anchoring membrane 2131 to be more easily and/or predictably pulled or collapsed.

Cuff 2100 may include a lower esophageal sphincter (LES) portion 2140.

LES portion 2140 may include an LES liner 2141. LES liner 2141 may be coupled to distal portion 2131$d$ of anchoring membrane 2131.

LES liner 2141 may be configured to be placed through the LES. LES liner 2141 may be configured to allow the LES to close normally. LES liner 2141 may be thinner and/or more flexible than capture liner 2121 and/or anchoring membrane 2131.

LES liner 2141 may include one or more layers. LES liner 2141 may be at least semi-permeable to food and/or liquids. LES liner 2141 may be made of silicone, polyethylene, polypropylene, a polyurethane such as PELLETHANE, DACRON, a woven material, a mesh material, or other suitable material.

Capture liner 2121, anchoring membrane 2131, and LES liner 2141 may have the same or different properties. Capture liner 2121, anchoring membrane 2131, and LES liner 2141 may be made of the same or different materials and/or thicknesses.

Attachment structure 2125 and reinforcement structure 2135 may have the same or different properties. Attachment structure 2125 and reinforcement structure 2135 may be made of the same or different materials and/or thicknesses.

Any combination of capture liner 2121, anchoring membrane 2131, LES liner 2141, attachment structure 2125, and reinforcement structure 2135 may be formed as one or more pieces. For example, capture liner 2121 and attachment structure 2125 may be formed as a single piece.

Capture liner 2121, anchoring membrane 2131, and LES liner 2141 may have the same or different widths. Capture liner 2121 may have a width the same as or greater than anchoring membrane 2131 and/or LES liner 2141. Anchoring membrane 2131 may have a width the same as or greater than LES liner 2141. LES liner 2141 with a width smaller than capture liner 2121 and/or anchoring membrane 2131 may act as a restriction device, and may contribute to a sense of fullness. LES liner 2141 with a width smaller than capture liner 2121 and/or anchoring membrane 2131 may push capture liner 2121 and/or anchoring membrane 2131 in a proximal direction when the LES closes and help keep cuff 2100 in place.

Capture liner 2121, anchoring membrane 2131, and LES liner 2141 may each have a length of approximately 10 mm to 40 mm. Capture liner 2121, anchoring membrane 2131, and LES liner 2141 may have widths of approximately 15 mm to 35 mm. For example, capture liner 2121 may have a width of approximately 25 mm, anchoring membrane 2131 may have a width of approximately 22 mm, and LES liner 2141 may have a width of approximately 15 mm.

Cuff 2100 may include one or more drawstrings 2152. Drawstrings 2152 may be coupled to one or more of capture liner 2121, anchoring membrane 2131, and LES liner 2141. Drawstrings 2152 may be at least partially coupled around one or more of capture liner 2121, anchoring membrane 2131, and LES liner 2141. Drawstrings 2152 may be configured to reduce a width of one or more of capture liner 2121, anchoring membrane 2131, and LES liner 2141 for delivery and/or removal of cuff 2100. Drawstrings 2152 may be removable or non-removable. One or more drawstrings 2152 may include a loose portion forming a loop 2152' which may facilitate grasping drawstring 2152.

Cuff 2100 may include at least one stiffening member 2154. Stiffening member 2154 may be coupled along at least a portion of a length of cuff 2100. Stiffening member 2154 may be configured to reduce the likelihood of cuff 2100 inverting. Stiffening member 2154 may be bonded to one or more of capture liner 2121, anchoring membrane 2131, and LES liner 2141. Stiffening member 2154 may be elongate. Stiffening member 2154 be made of metal, plastic, or other suitable material. Stiffening member 2154 may be radiopaque.

Cuff 2100 may include one or more tissue ingrowth elements 2180. Tissue ingrowth elements 2180 may be configured to allow the wall of the esophagus to grow into cuff 2100.

Tissue ingrowth elements 2180 may include conformance structure 2127 such as stent 2128 coupled to an outside of capture liner 2121. Tissue ingrowth elements 2180 may include at least one additional stent 2128 coupled to an outside of anchoring membrane 2131 and/or LES liner 2141. Stent 2128 may be configured to allow tissue ingrowth. Stent 2128 may have openings configured to allow tissue ingrowth.

Figure 3A:
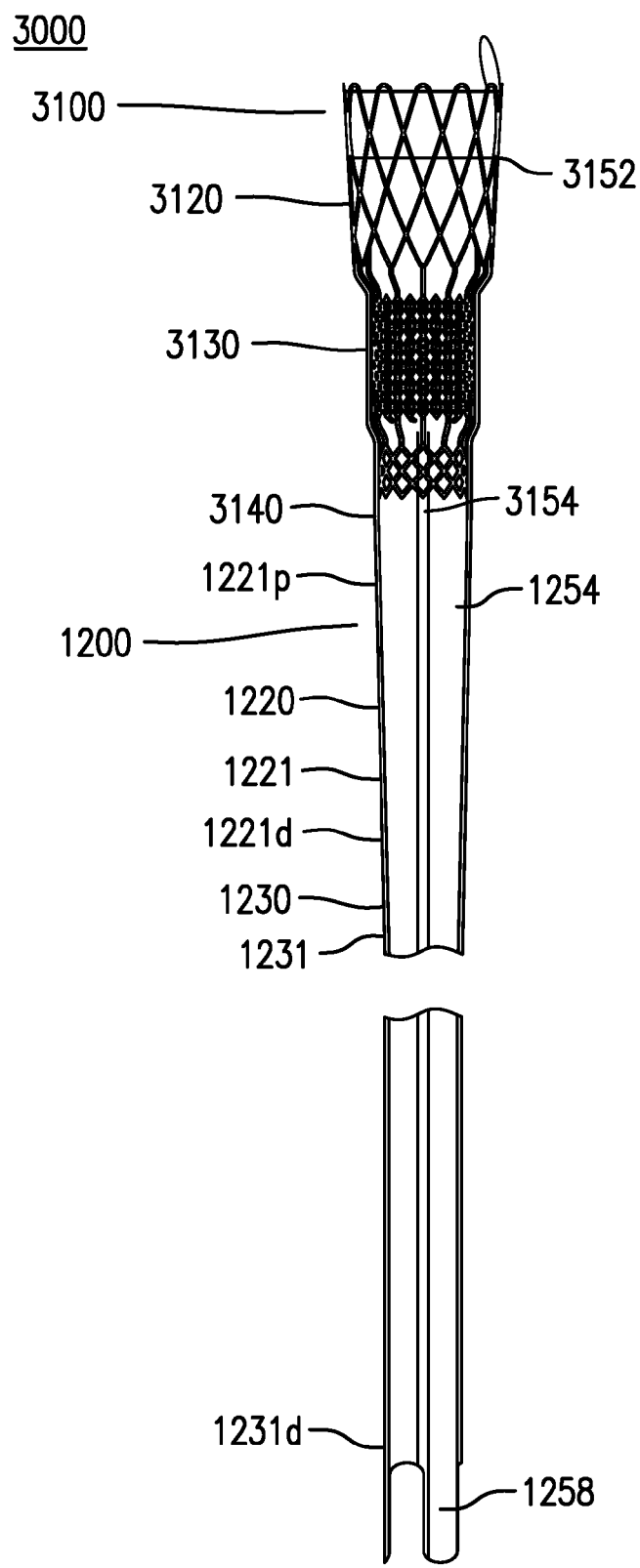
FIGS. 3A-3B show another embodiment of a gastrointestinal bypass device 3000.
Figure 3B:
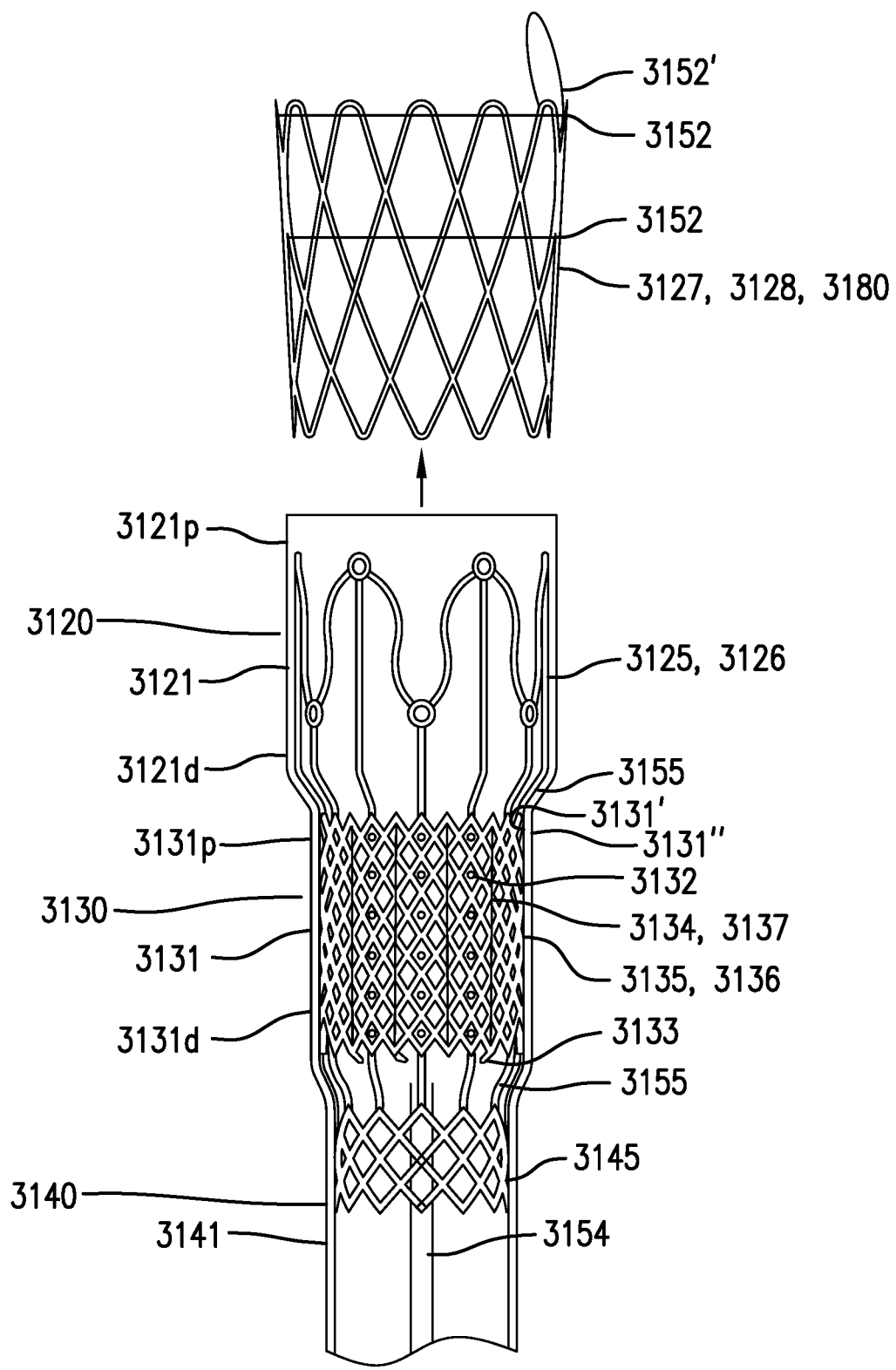

FIGS. 3A-3B show another embodiment of a gastrointestinal bypass device 3000. FIG. 3A shows a side view of gastrointestinal bypass device 3000. FIG. 3B shows an exploded view of cuff 3100 of gastrointestinal bypass device 3000.

Gastrointestinal bypass device 3000 may be configured to receive swallowed food in the esophagus and bypass the food into the intestine.

Gastrointestinal bypass device 3000 may include a cuff 3100.

Cuff 3100 may include a capture portion 3120.

Capture portion 3120 may include a capture liner 3121. Capture liner 3121 may include a proximal portion 3121$p$ and a distal portion 3121$d$.

Capture liner 3121 may be configured to be placed in the esophagus. Capture liner 3121 may be configured to capture or receive swallowed food in the esophagus so that the food may be bypassed into the intestine. Capture liner 3121 may be configured to conform to the inside of the esophagus to reduce the amount of food that is not captured and bypassed. Capture liner 3121 may have an outward bias configured to conform to the inside of the esophagus. Capture liner 3121 may have an outward bias that is not sufficient to retain cuff 3100 in the esophagus.

Capture liner 3121 may be funnel-shaped, with proximal portion 3121$p$ having a width greater than distal portion 3121$d$. Alternatively, capture liner 3121 may have a width that is constant.

Capture liner 3121 may be configured to reduce its impact on the ability of the esophagus to open and close. Capture liner 3121 may be flexible.

Capture liner 3121 may include one or more layers. Capture liner 3121 may be at least semi-permeable to food and/or liquids. Capture liner 3121 may be made of silicone, polyethylene, polypropylene, a polyurethane such as PELLETHANE, DACRON, a woven material, a mesh material, or other suitable material.

Capture portion 3120 may include a conformance structure 3127. Conformance structure 3127 may be coupled to capture liner 3121.

Conformance structure 3127 may be configured to enhance conformance of capture liner 3121 to the inside of the esophagus. Conformance structure 3127 may have an outward bias configured to enhance conformance of capture liner 3121 to the inside of the esophagus. Conformance structure 3127 may have an outward bias that is not sufficient to retain capture cuff 3100 in the esophagus.

Conformance structure 3127 may include a stent 3128. Stent 3128 may be made of metal, plastic, or other suitable material. Conformance structure 3127 may include a mesh, a braid, or other suitable structure.

Conformance structure 3127 may be coupled to an outside of capture liner 3121. Conformance structure 3127 may be coupled to capture liner 3121 with sutures or other suitable method.

Capture portion 3120 may include an attachment structure 3125. Attachment structure 3125 may be coupled to capture liner 3121.

Attachment structure 3125 may be configured to facilitate coupling conformance structure 3127 to capture liner 3121. Attachment structure 3125 may provide a structure to which conformance structure 3127 may be sutured and/or otherwise coupled.

Attachment structure 3125 may include a wave-like structure 3126. Wave-like structure 3126 may include any one or any combination of eyelets, clips, posts, and other features to facilitate coupling such as suturing of conformance structure 3127. Wave-like structure 3126 may be made of plastic, metal, or other suitable material. Attachment structure 3125 may include a braid, a stent, a mesh, or other suitable structure.

Attachment structure 3125 may be coupled between two layers of capture liner 3121. Attachment structure 3125 may be coupled between two layers of capture liner 3121 blow molded to sandwich attachment structure 3125. Attachment structure 3125 may provide a substrate on which at least a portion of capture liner 3121 is formed, such as by dip coating, spray coating, or other suitable methods.

Cuff 3100 includes an anchoring portion 3130.

Anchoring portion 3130 may include an anchoring membrane 3131. Anchoring membrane 3131 may include a proximal portion 3131$p$ and a distal portion 3131$d$. Anchoring membrane 3131 may be coupled to distal portion 3121$d$ of capture liner 3121. Alternatively, anchoring membrane 3131 may be coupled to proximal portion 3121$p$ of capture liner 3121.

Anchoring membrane 3131 may be configured to be placed in the esophagus. Anchoring membrane 3131 may be configured to be placed next to a wall of the esophagus. Anchoring membrane 3131 may be configured to be attached to a tissue anchor. Anchoring membrane 3131 may be configured to be attached to the wall of the esophagus with a tissue anchor placed through anchoring membrane 3131. Anchoring membrane 3131 may be configured to be pierced to allow a tissue anchor to be placed through anchoring membrane 3131 and attach anchoring membrane 3131 to the wall of the esophagus. Anchoring membrane 3131 may be configured to retain a tissue anchor placed through anchoring membrane 3131. Anchoring membrane 3131 may be sufficiently strong to prevent a tissue anchor placed through anchoring membrane from pulling through and/or tearing anchoring membrane 3131.

Anchoring membrane 3131 may be configured to be collapsible. Anchoring membrane 3131 may be configured to be pulled or collapsed with a vacuum applied to first side 3131' of anchoring membrane 3131. Anchoring membrane 3131 may be configured to be pulled or collapsed with a grasper or hook from first side 3131' of anchoring membrane 3131. Anchoring membrane 3131 may be configured to be pulled or collapsed toward first side 3131' of anchoring membrane 3131.

Anchoring membrane 3131 may be configured to reduce its impact on the ability of the esophagus to open and close. Anchoring membrane 3131 may be flexible. Anchoring membrane 3131 may be stretchable and recover without permanent set.

Anchoring membrane 3131 may include one or more layers. Anchoring membrane 3131 may be at least semi-permeable to food and/or liquids. Anchoring membrane 3131 may be made of silicone, polyethylene, polypropylene, a polyurethane such as PELLETHANE, DACRON, a woven material, a mesh material, or other suitable material.

Anchoring membrane 3131 may include one or more perforations 3132 formed in anchoring membrane 3131.

Perforations 3132 may be configured to allow at least a portion of a vacuum applied to one side of anchoring membrane 3131 to reach through anchoring membrane 3131. Perforations 3132 may be configured to allow at least a portion of a vacuum applied to anchoring membrane 3131 to reach a tissue wall placed next to anchoring membrane 3131. Perforations 3132 may be configured to allow at least a portion of a vacuum applied to first side 3131' of anchoring membrane 3131 to reach a tissue wall placed next to second side 3131" of anchoring membrane 3131.

Perforations 3132 may include any one or any combination of holes, slits, and other openings of any suitable shape and size.

Anchoring membrane 3131 may include one or more pulls 3133. Pulls 3133 may be coupled to anchoring membrane 3131 and/or reinforcement structure 3135. Pulls 3133 may extend from first side 3131' of anchoring membrane 3131.

Pulls 3133 may be configured to allow anchoring membrane 3131 to be pulled or collapsed. Pulls 3133 may be configured to allow anchoring membrane 3131 to be pulled or collapsed toward first side 3131' of anchoring membrane 3131.

Pulls 3133 may include any one or any combination of loops, tabs, and other suitable structures. Pulls 3133 may be made of a biodegradable material.

Anchoring membrane 3131 may include one or more creases 3134. Creases 3134 may be formed by scoring anchoring membrane 3131 and/or forming thinner portions of anchoring membrane 3131. Creases 3134 may be configured to allow anchoring membrane 3131 to collapse along creases 3134. Creases 3134 may allow anchoring membrane 3131 to be more easily and/or predictably pulled or collapsed.

Anchoring portion 3130 may include a reinforcement structure 3135. Reinforcement structure 3135 may be coupled to anchoring membrane 3131.

Reinforcement structure 3135 may be configured to reinforce anchoring membrane 3131. Reinforcement structure 3135 may be configured to retain a tissue anchor placed through reinforcement structure 3135. Reinforcement structure 3135 may be configured to reduce the likelihood of a tissue anchor placed through anchoring membrane 3131 pulling through and/or tearing anchoring membrane 3131.

Reinforcement structure 3135 may include a braid 3136. Braid 3136 may have uniform or varying opening sizes. Braid 3136 may be made of plastic, metal, or other suitable material. Reinforcement structure 3135 may include a stent, mesh, or other suitable structure.

Reinforcement structure 3135 may be coupled between two layers of anchoring membrane 3131. Reinforcement structure 3135 may be coupled between two layers of anchoring membrane 3131 blow molded to sandwich reinforcement structure 3135. Reinforcement structure 3135 may provide a substrate on which at least a portion of anchoring membrane 3131 is formed, such as by dip coating, spray coating, or other suitable methods.

Anchoring membrane 3131 may include one or more creases 3137. Creases 3137 may be formed by scoring anchoring membrane 3131 and/or forming thinner portions of anchoring membrane 3131. Creases 3137 may be configured to allow anchoring membrane 3131 to collapse along creases 3137. Creases 3137 may allow anchoring membrane 3131 to be more easily and/or predictably pulled or collapsed.

Reinforcement structure 3135 may be coupled to distal portion 3125$d$ of attachment structure 3125. Reinforcement structure 3135 may be coupled to distal portion 3125$d$ of attachment structure 3125 with one or more connecting members 3155.

Connecting members 3155 may be configured to allow attachment structure 3125 and reinforcement structure 3135 to move with respect to each other. Connecting members 3155 may be configured to reduce forces transferred between attachment structure 3125 and reinforcement structure 3135. Connecting members 3155 may include straight and/or curved portions.

Cuff 3100 may include a lower esophageal sphincter (LES) portion 3140.

LES portion 3140 may include an LES liner 3141. LES liner 3141 may be coupled to distal portion 3131$d$ of anchoring membrane 3131.

LES liner 3141 may be configured to be placed through the LES. LES liner 3141 may be configured to allow the LES to close normally. LES liner 3141 may be thinner and/or more flexible than capture liner 3121 and/or anchoring membrane 3131.

LES liner 3141 may include one or more layers. LES liner 3141 may be at least semi-permeable to food and/or liquids. LES liner 3141 may be made of silicone, polyethylene, polypropylene, a polyurethane such as PELLETHANE, DACRON, a woven material, a mesh material, or other suitable material.

LES portion 3140 may include a support structure 3145. Support structure 3145 may be coupled to a proximal portion 3141$p$ of LES liner 3141.

Support structure 3145 may be configured to provide a transition to a sleeve.

Support structure 3145 may include a braid 3146. Braid 3146 may be made of plastic, metal, or other suitable material. Braid 3146 may have uniform or varying opening sizes. Support structure 3145 may include a stent, a mesh, or other suitable structure.

Support structure 3145 may be coupled between two layers of LES liner 3141. Support structure 3145 may be coupled between two layers of LES liner 3141 blow molded to sandwich support structure 3145. Support structure 3145 may provide a substrate on which at least a portion of LES liner 3141 is formed, such as by dip coating, spray coating, or other suitable methods.

Support structure 3145 may be coupled to a distal portion 3135$d$ of reinforcement structure 3135. Support structure 3145 may be coupled to distal portion 3135$d$ of reinforcement structure 3135 with one or more connecting members 3155.

Connecting members 3155 may be configured to allow reinforcement structure 3135 and support structure 3145 to move with respect to each other. Connecting members 3155 may be configured to reduce forces transferred between reinforcement structure 3135 and support structure 3145. Connecting members 3155 may include straight and/or curved portions.

Capture liner 3121, anchoring membrane 3131, and LES liner 3141 may have the same or different properties. Capture liner 3121, anchoring membrane 3131, and LES liner 3141 may be made of the same or different materials and/or thicknesses.

Attachment structure 3125, reinforcement structure 3135, support structure 3145, and connecting members 3155 may have the same or different properties. Attachment structure 3125, reinforcement structure 3135, support structure 3145, and connecting members 3155 may be made of the same or different materials and/or thicknesses.

Any combination of capture liner 3121, anchoring membrane 3131, LES liner 3141, attachment structure 3125, reinforcement structure 3135, support structure 3145, and connecting members 3155 may be formed as one or more pieces. For example, attachment structure 3125, reinforcement structure 3135, support structure 3145, and connecting members 3155 may be molded or 3D printed as a single piece.

Capture liner 3121, anchoring membrane 3131, and LES liner 3141 may have the same or different widths. Capture liner 3121 may have a width the same as or greater than anchoring membrane 3131 and/or LES liner 3141. Anchoring membrane 3131 may have a width the same as or greater than LES liner 3141. LES liner 3141 with a width smaller than capture liner 3121 and/or anchoring membrane 3131 may act as a restriction device, and may contribute to a sense of fullness. LES liner 3141 with a width smaller than capture liner 3121 and/or anchoring membrane 3131 may push capture liner 3121 and/or anchoring membrane 3131 in a proximal direction when the LES closes and help keep cuff 3100 in place.

Capture liner 3121, anchoring membrane 3131, and LES liner 3141 may each have a length of approximately 10 mm to 40 mm. Capture liner 3121, anchoring membrane 3131, and LES liner 3141 may have widths of approximately 15 mm to 35 mm. For example, capture liner 3121 may have a width of approximately 25 mm, anchoring membrane 3131 may have a width of approximately 22 mm, and LES liner 3141 may have a width of approximately 15 mm.

Cuff 3100 may include one or more drawstrings 3152. Drawstrings 3152 may be coupled to one or more of capture liner 3121, anchoring membrane 3131, and LES liner 3141. Drawstrings 3152 may be at least partially coupled around one or more of capture liner 3121, anchoring membrane 3131, and LES liner 3141. Drawstrings 3152 may be configured to reduce a width of one or more of capture liner 3121, anchoring membrane 3131, and LES liner 3141 for delivery and/or removal of cuff 3100. Drawstrings 3152 may be removable or non-removable. One or more drawstrings 3152 may include a loose portion forming a loop 3152' which may facilitate grasping drawstring 3152.

Cuff 3100 may include at least one stiffening member 3154. Stiffening member 3154 may be coupled along at least a portion of a length of cuff 3100. Stiffening member 3154 may be configured to reduce the likelihood of cuff 3100 inverting. Stiffening member 3154 may be bonded to one or more of capture liner 3121, anchoring membrane 4131, and LES liner 3141. Stiffening member 3154 may be elongate. Stiffening member 3154 be made of metal, plastic, or other suitable material. Stiffening member 3154 may be radiopaque.

Figure 4A:
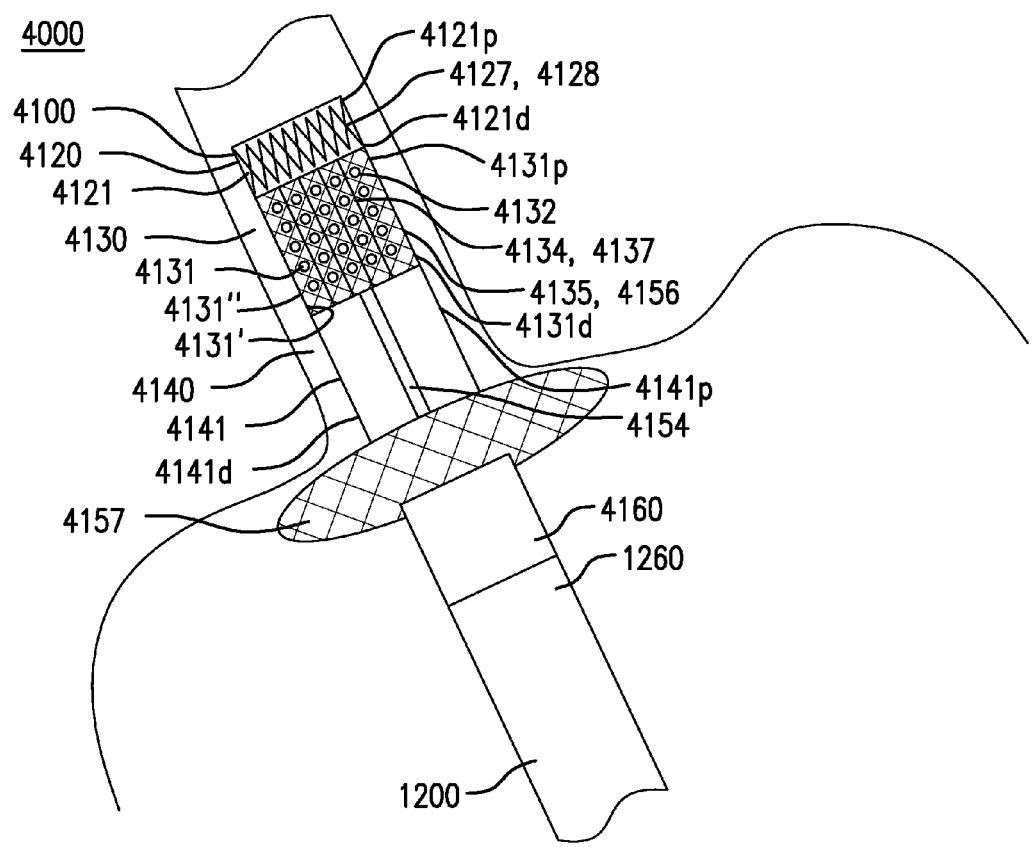
FIGS. 4A-4B show another embodiment of a gastrointestinal bypass device 4000.
Figure 4B:
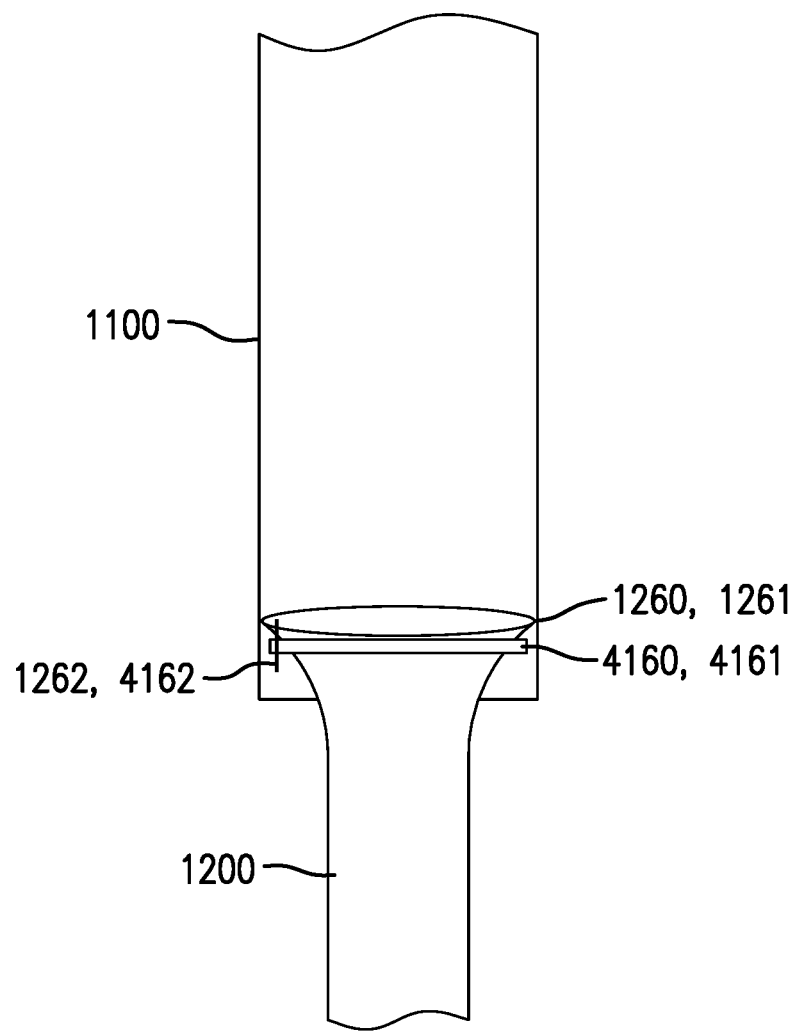

FIGS. 4A-4B show another embodiment of a gastrointestinal bypass device 4000. FIG. 4A shows a side view of gastrointestinal bypass device 4000. FIG. 4B shows an enlarged view of cuff-to-sleeve coupling 4160 and sleeve-to-cuff coupling 1260.

Gastrointestinal bypass device 4000 may be configured to receive swallowed food in the esophagus and bypass the food into the intestine.

Gastrointestinal bypass device 4000 may include a cuff 4100.

Cuff 4100 may include a capture portion 4120.

Capture portion 4120 may include a capture liner 4121. Capture liner 4121 may include a proximal portion 4121*p* and a distal portion 4121*d*.

Capture liner 4121 may be configured to be placed in the esophagus. Capture liner 4121 may be configured to capture or receive swallowed food in the esophagus so that the food may be bypassed into the intestine. Capture liner 4121 may be configured to conform to the inside of the esophagus to reduce the amount of food that is not captured and bypassed. Capture liner 4121 may have an outward bias configured to conform to the inside of the esophagus. Capture liner 4121 may have an outward bias that is not sufficient to retain cuff 4100 in the esophagus.

Capture liner 4121 may be funnel-shaped, with proximal portion 4121*p* having a width greater than distal portion 4121*d*. Alternatively, capture liner 4121 may have a width that is constant.

Capture liner 4121 may be configured to reduce its impact on the ability of the esophagus to open and close. Capture liner 4121 may be flexible.

Capture liner 4121 may include one or more layers. Capture liner 4121 may be at least semi-permeable to food and/or liquids. Capture liner 4121 may be made of silicone, polyethylene, polypropylene, a polyurethane such as PELLETHANE, DACRON, a woven material, a mesh material, or other suitable material.

Capture portion 4120 may include a conformance structure 4127. Conformance structure 4127 may be coupled to capture liner 4121.

Conformance structure 4127 may be configured to enhance conformance of capture liner 4121 to the inside of the esophagus. Conformance structure 4127 may have an outward bias configured to enhance conformance of capture liner 4121 to the inside of the esophagus. Conformance structure 4127 may have an outward bias that is not sufficient to retain capture cuff 4100 in the esophagus.

Conformance structure 4127 may include a stent 4128. Stent 4128 may be made of metal, plastic, or other suitable material. Conformance structure 4127 may include a mesh, a braid, or other suitable structure.

Conformance structure 4127 may be coupled to an outside of capture liner 4121. Conformance structure 4127 may be coupled to capture liner 4121 with sutures or other suitable method. Alternatively, conformance structure 4127 may be coupled between two layers of capture liner 4121. Conformance structure 4127 may be coupled between two layers of capture liner 4121 blow molded to sandwich conformance structure 4127.

Capture portion 4120 may include an attachment structure 4125. Attachment structure 4125 may be coupled to capture liner 4121.

Attachment structure 4125 may be configured to facilitate coupling conformance structure 4127 to capture liner 4121. Attachment structure 4125 may provide a structure to which conformance structure 4127 may be sutured and/or otherwise coupled.

Attachment structure 4125 may include a braid 4126. Braid 4126 may be made of plastic, metal, or other suitable material. Braid 4126 may have uniform or varying opening sizes. Attachment structure 4125 may include a stent, a mesh, or other suitable structure.

Attachment structure 4125 may be coupled between two layers of capture liner 4121. Attachment structure 4125 may be coupled between two layers of capture liner 4121 blow molded to sandwich attachment structure 4125. Attachment structure 4125 may provide a substrate on which at least a portion of capture liner 4121 is formed, such as by dip coating, spray coating, or other suitable methods.

Cuff 4100 includes an anchoring portion 4130.

Anchoring portion 4130 may include an anchoring membrane 4131. Anchoring membrane 4131 may include a proximal portion 4131*p* and a distal portion 4131*d*. Anchoring membrane 4131 may be coupled to distal portion 4121*d* of capture liner 4121. Alternatively, anchoring membrane 4131 may be coupled to proximal portion 4121*p* of capture liner 4121.

Anchoring membrane 4131 may be configured to be placed in the esophagus. Anchoring membrane 4131 may be configured to be placed next to a wall of the esophagus. Anchoring membrane 4131 may be configured to be attached to a tissue anchor. Anchoring membrane 4131 may be configured to be attached to the wall of the esophagus with a tissue anchor placed through anchoring membrane 4131. Anchoring membrane 4131 may be configured to be pierced to allow a tissue anchor to be placed through anchoring membrane 4131 and attach anchoring membrane 4131 to the wall of the esophagus. Anchoring membrane 4131 may be configured to retain a tissue anchor placed through anchoring membrane 4131. Anchoring membrane 4131 may be sufficiently strong to prevent a tissue anchor placed through anchoring membrane from pulling through and/or tearing anchoring membrane 4131.

Anchoring membrane 4131 may be configured to be collapsible. Anchoring membrane 4131 may be configured to be pulled or collapsed with a vacuum applied to first side 4131' of anchoring membrane 4131. Anchoring membrane 4131 may be configured to be pulled or collapsed with a grasper or hook from first side 4131' of anchoring membrane 4131. Anchoring membrane 4131 may be configured to be pulled or collapsed toward first side 4131' of anchoring membrane 4131.

Anchoring membrane 4131 may be configured to reduce its impact on the ability of the esophagus to open and close. Anchoring membrane 4131 may be flexible. Anchoring membrane 4131 may be stretchable and recover without permanent set.

Anchoring membrane 4131 may include one or more layers. Anchoring membrane 4131 may be at least semi-permeable to food and/or liquids. Anchoring membrane 4131 may be made of silicone, polyethylene, polypropylene, a polyurethane such as PELLETHANE, DACRON, a woven material, a mesh material, or other suitable material.

Anchoring membrane 4131 may include one or more perforations 4132 formed in anchoring membrane 4131.

Perforations 4132 may be configured to allow at least a portion of a vacuum applied to one side of anchoring membrane 4131 to reach through anchoring membrane 4131. Perforations 4132 may be configured to allow at least a portion of a vacuum applied to anchoring membrane 4131 to reach a tissue wall placed next to anchoring membrane 4131. Perforations 4132 may be configured to allow at least a portion of a vacuum applied to first side 4131' of anchoring membrane 4131 to reach a tissue wall placed next to second side 4131" of anchoring membrane 4131.

Perforations 4132 may include any one or any combination of holes, slits, and other openings of any suitable shape and size.

Anchoring membrane 4131 may include one or more pulls 4133. Pulls 4133 may be coupled to anchoring membrane 4131 and/or reinforcement structure 4135. Pulls 4133 may extend from first side 4131' of anchoring membrane 4131.

Pulls 4133 may be configured to allow anchoring membrane 4131 to be pulled or collapsed. Pulls 4133 may be configured to allow anchoring membrane 4131 to be pulled or collapsed toward first side 4131' of anchoring membrane 4131.

Pulls 4133 may include any one or any combination of loops, tabs, and other suitable structures. Pulls 4133 may be made of a biodegradable material.

Anchoring membrane 4131 may include one or more creases 4134. Creases 4134 may be formed by scoring anchoring membrane 4131 and/or forming thinner portions of anchoring membrane 4131. Creases 4134 may be configured to allow anchoring membrane 4131 to collapse along creases 4134. Creases 4134 may allow anchoring membrane 4131 to be more easily and/or predictably pulled or collapsed.

Anchoring portion 4130 may include a reinforcement structure 4135. Reinforcement structure 4135 may be coupled to anchoring membrane 4131.

Reinforcement structure 4135 may be configured to reinforce anchoring membrane 4131. Reinforcement structure 4135 may be configured to retain a tissue anchor placed through reinforcement structure 4135. Reinforcement structure 4135 may be configured to reduce the likelihood of a tissue anchor placed through anchoring membrane 4131 pulling through and/or tearing anchoring membrane 4131.

Reinforcement structure 4135 may include a braid 4136. Braid 4136 may have uniform or varying opening sizes. Braid 4136 may be made of plastic, metal, or other suitable material. Reinforcement structure 4135 may include a stent, mesh, or other suitable structure.

Reinforcement structure 4135 may be coupled between two layers of anchoring membrane 4131. Reinforcement structure 4135 may be coupled between two layers of anchoring membrane 4131 blow molded to sandwich reinforcement structure 4135. Reinforcement structure 4135 may provide a substrate on which at least a portion of anchoring membrane 4131 is formed, such as by dip coating, spray coating, or other suitable methods.

Anchoring membrane 4131 may include one or more creases 4137. Creases 4137 may be formed by scoring anchoring membrane 4131 and/or forming thinner portions of anchoring membrane 4131. Creases 4137 may be configured to allow anchoring membrane 4131 to collapse along creases 4137. Creases 4137 may allow anchoring membrane 4131 to be more easily and/or predictably pulled or collapsed.

Cuff 4100 may include a lower esophageal sphincter (LES) portion 4140.

LES portion 4140 may include an LES liner 4141. LES liner 4141 may be coupled to distal portion 4131d of anchoring membrane 4131.

LES liner 4141 may be configured to be placed through the LES. LES liner 4141 may be configured to allow the LES to close normally. LES liner 4141 may be thinner and/or more flexible than capture liner 4121 and/or anchoring membrane 4131.

LES liner 4141 may include one or more layers. LES liner 4141 may be at least semi-permeable to food and/or liquids. LES liner 4141 may be made of silicone, polyethylene, polypropylene, a polyurethane such as PELLETHANE, DACRON, a woven material, a mesh material, or other suitable material.

Capture liner 4121, anchoring membrane 4131, and LES liner 4141 may have the same or different properties. Capture liner 4121, anchoring membrane 4131, and LES liner 4141 may be made of the same or different materials and/or thicknesses.

Attachment structure 4125 and reinforcement structure 4135 may have the same or different properties. Attachment structure 4125 and reinforcement structure 4135 may be made of the same or different materials and/or thicknesses.

Any combination of capture liner 4121, anchoring membrane 4131, LES liner 4141, attachment structure 4125, and reinforcement structure 4135 may be formed as one or more pieces. For example, capture liner 4121 and attachment structure 4125 may be formed as a single piece.

Capture liner 4121, anchoring membrane 4131, and LES liner 4141 may have the same or different widths. Capture liner 4121 may have a width the same as or greater than anchoring membrane 4131 and/or LES liner 4141. Anchoring membrane 4131 may have a width the same as or greater than LES liner 4141. LES liner 4141 with a width smaller than capture liner 4121 and/or anchoring membrane 4131 may act as a restriction device, and may contribute to a sense of fullness. LES liner 4141 with a width smaller than capture liner 4121 and/or anchoring membrane 4131 may push capture liner 4121 and/or anchoring membrane 4131 in a proximal direction when the LES closes and help keep cuff 4100 in place.

Capture liner 4121, anchoring membrane 4131, and LES liner 4141 may each have a length of approximately 10 mm to 40 mm. Capture liner 4121, anchoring membrane 4131, and LES liner 4141 may have widths of approximately 15 mm to 35 mm. For example, capture liner 4121 may have a width of approximately 25 mm, anchoring membrane 4131 may have a width of approximately 22 mm, and LES liner 4141 may have a width of approximately 15 mm.

Cuff 4100 may include one or more drawstrings 4152. Drawstrings 4152 may be coupled to one or more of capture liner 4121, anchoring membrane 4131, and LES liner 4141. Drawstrings 4152 may be at least partially coupled around one or more of capture liner 4121, anchoring membrane 4131, and LES liner 4141. Drawstrings 4152 may be configured to reduce a width of one or more of capture liner 4121, anchoring membrane 4131, and LES liner 4141 for delivery and/or removal of cuff 4100. Drawstrings 4152 may be removable or non-removable. One or more drawstrings 4152 may include a loose portion forming a loop 4152' which may facilitate grasping drawstring 4152.

Cuff 4100 may include at least one stiffening member 4154. Stiffening member 4154 may be coupled along at least a portion of a length of cuff 4100. Stiffening member 4154 may be configured to reduce the likelihood of cuff 4100 inverting. Stiffening member 4154 may be bonded to one or more of capture liner 4121, anchoring membrane 4131, and LES liner 4141. Stiffening member 4154 may be elongate. Stiffening member 4154 be made of metal, plastic, or other suitable material. Stiffening member 4154 may be radiopaque.

Cuff 4100 may include a widened portion 4157. Widened portion 4157 may be coupled to a distal portion 4141*d* of LES liner 4141. Widened portion 4157 may be configured to reduce the likelihood of cuff 4100 inverting. Widened portion 4157 may include an expandable and/or inflatable structure.

Widened portion 4157 may have a width of approximately 40 mm to 50 mm.

Cuff 4100 may include a cuff-to-sleeve coupling 4160. Cuff-to-sleeve coupling 4160 may be configured to be coupled to a sleeve-to-cuff coupling of a sleeve. Cuff-to-sleeve coupling 4160 may include a flange 4161 coupled to an inside of a distal portion 4141*d* of LES liner 4141. Cuff-to-sleeve coupling 4160 may include one or more sutures 4162

Gastrointestinal bypass devices 1000, 2000, 3000, and 4000 may include a sleeve 1200. Gastrointestinal bypass devices 1000, 2000, 3000, and 4000 may include any of the sleeves or tubes described in U.S. patent application publication no. 2015/0018745, which is incorporated by reference.

Sleeve 1200 may include a gastric portion 1220.

Gastric portion 1220 may include a gastric liner 1221. Gastric liner 1221 may include a proximal portion 1221*p* and a distal portion 1221*d*. Gastric liner 1221 may be coupled to a distal portion of an LES liner.

Gastric liner 1221 may be configured to be placed at least partially in the stomach. Gastric liner 1221 may be configured to bypass food into the intestine.

Gastric liner 1221 may be made of silicone, polyethylene, polypropylene, a polyurethane such as PELLETHANE, DACRON, a woven material, a mesh material, or other suitable material. Gastric liner 1221 may include one or more coatings to provide desired properties including resisting calcification, delivering medications, and providing lubriciousness. Coatings may include parylene, polyvinypyrrolidone (PVP), and other suitable materials.

Gastric liner 1221 may have a length of approximately 200 mm to 350 mm. Gastric liner 1221 may have a width of approximately 15 mm to 100 mm.

Gastric liner 1221 may be configured to allow peristaltic forces to act on its contents. Gastric liner 1221 may be flexible.

Sleeve 1200 may include an intestinal portion 1230.

Intestinal portion 1230 may include an intestinal liner 1231. Intestinal liner 1231 may be coupled to distal portion 1221*d* of gastric liner 1221.

Intestinal liner 1231 may be configured to be placed at least partially in the intestine. Intestinal liner 1231 may be configured to bypass food into the intestine.

Intestinal liner 1231 may be made of silicone, polyethylene, polypropylene, a polyurethane such as PELLETHANE, DACRON, a woven material, a mesh material, or other suitable material. Intestinal liner 1231 may include one or more coatings to provide desired properties including resisting calcification, delivering medications, and providing lubriciousness. Coatings may include parylene, polyvinypyrrolidone (PVP), and other suitable materials.

Intestinal liner 1231 may have a length of approximately 150 mm to 4500 mm. Intestinal liner 1231 may have a width of approximately 15 mm to 40 mm.

Intestinal liner 1231 may be configured to allow peristaltic forces to act on its contents. Intestinal liner 1231 may be flexible. Intestinal liner 1231 may be not stretchable.

Sleeve 1200 may include at least one stiffening member 1254. Stiffening member 1254 may be coupled along at least a portion of a length of sleeve 1200. Stiffening member 1254 may be configured to reduce the likelihood of sleeve 1200 inverting, kinking, or twisting. Stiffening member 1254 may be bonded to one or more of gastric liner 1221 and intestinal liner 1231. Stiffening member 1254 may be elongate. Stiffening member 1254 may be of uniform or varying width and/or thickness. Stiffening member 1254 may be radiopaque.

Gastric portion 1220 may include a support structure 1225. Support structure 1225 may be coupled to gastric liner 1221.

Support structure 1225 may be configured to prevent at least a portion of gastric liner 1221 from collapsing. Support structure 1225 may be configured to keep at least a portion of gastric liner 1221 at least partially open. This may facilitate the passage of food out of cuff and into sleeve 1200.

Support structure 1225 may include stiffening member 1254 configured in a nonlinear fashion for at least a portion of gastric liner 1221. Stiffening member 1254 may be configured in a spiral or coiled fashion. Stiffening member 1254 may be configured as one or more circumferential rings. Stiffening member 1254 may be configured in a meandering fashion. Stiffening member 1254 may be thinner or thicker, and/or narrower or wider.

Support structure 1225 may include a braid. The braid may have uniform or varying opening sizes. The braid may be made of plastic, metal, or other suitable material. Support structure 1225 may include a stent, mesh, or other suitable structure.

Sleeve 1200 may include one or more tails 1258. Tails 1258 may be formed at a distal portion 1231*d* of intestinal liner 1231. Tails 1258 may allow distal portion 1231*d* of intestinal liner 1231 to be temporarily closed during delivery of sleeve 1200.

Sleeve 1200 may include a sleeve-to-cuff-coupling 1260. Sleeve-to-cuff coupling 1260 may be configured to be coupled to a cuff-to-sleeve coupling of a cuff. Sleeve-to-cuff coupling 1260 may include a flange 1261 coupled to proximal portion 1221*p* of gastric liner 1221. Flange 1261 may be configured to be deformable. Flange 1261 may be configured to be passed through and placed above flange 4161. Sleeve-to-cuff coupling 1260 may include one or more sutures 1262.

Sleeve 1200 and a cuff may be formed as one or more pieces.

Stiffening member 1254 of sleeve 1200 and a stiffening member of a cuff may be formed as one or more pieces.

A cuff may be used as a restriction device and/or a GERD device by using sleeve 1200 with a short length, or no sleeve at all. For example, sleeve 1200 may have a length of 50 mm to 300 mm.

Gastrointestinal bypass devices 1000, 2000, 3000, and 4000 may include any one or any combination of tissue anchors 1300, 2300, and 3300. Gastrointestinal bypass devices 1000, 2000, 3000, and 4000 may include any of the tissue anchors described in U.S. patent application publication nos. 2009/0012541 and 2015/0018745, both of which are incorporated by reference.

Figure 5A:
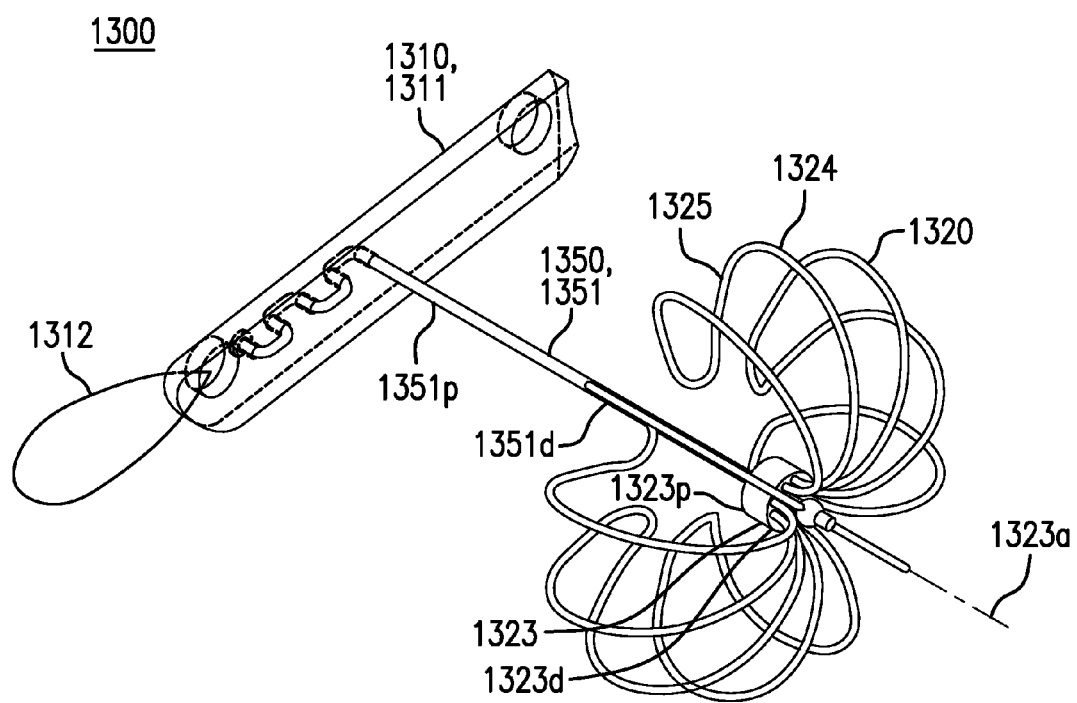
FIGS. 5A-5C show two embodiments of a tissue anchor 1300.
Figure 5B:
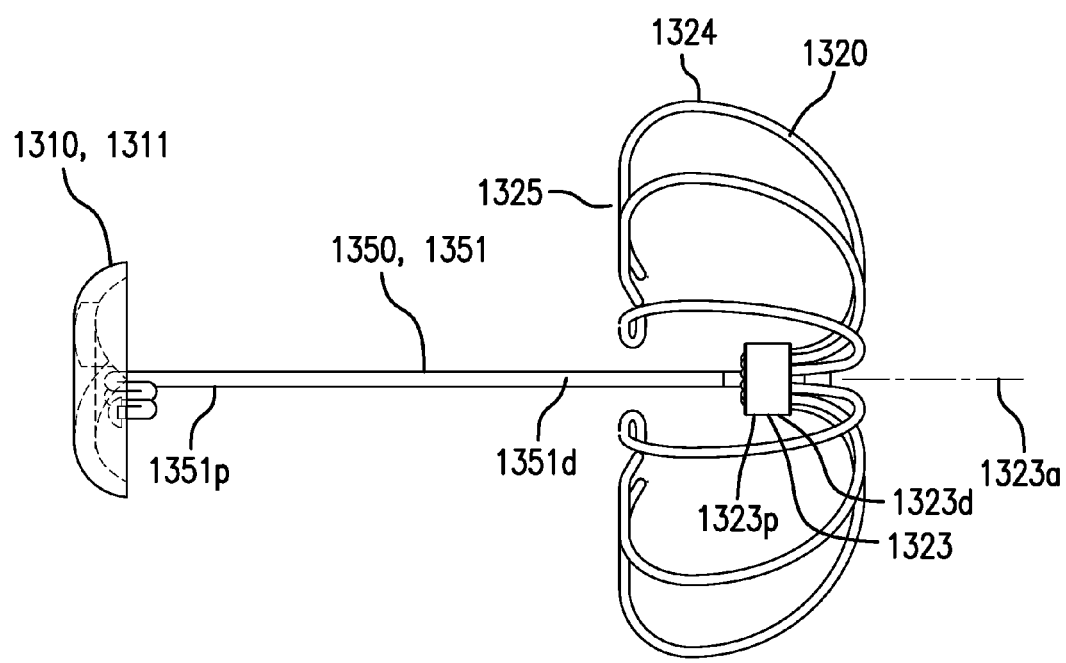
Figure 5C:
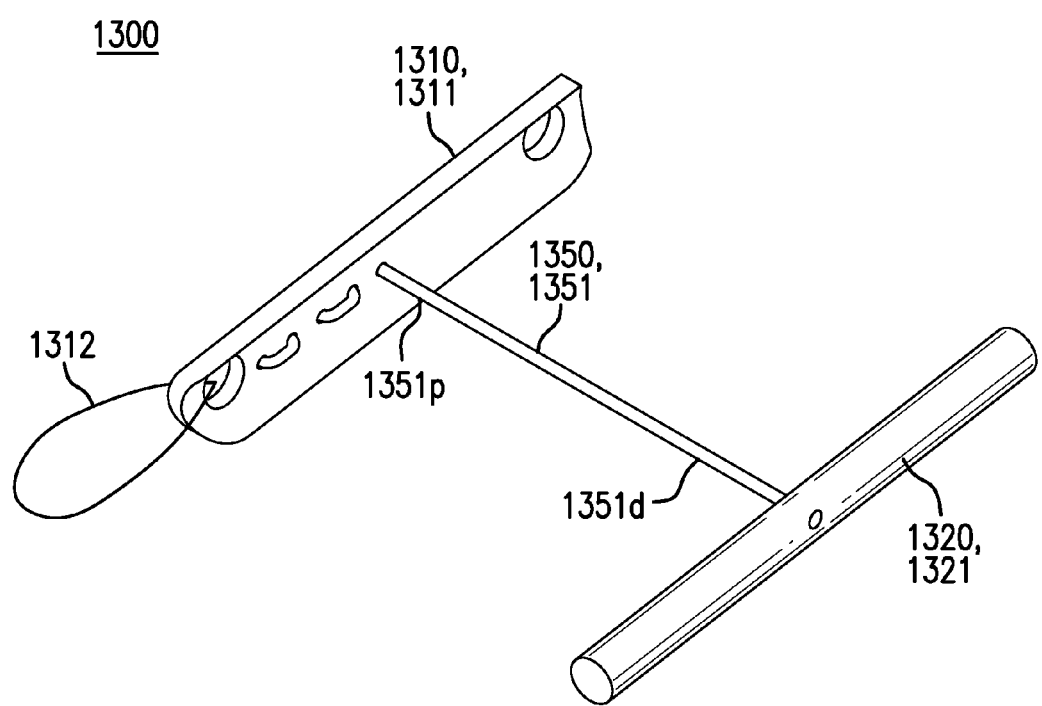

FIGS. 5A-5C show embodiments of a tissue anchor 1300. FIGS. 5A-5B show perspective and side views, respectively, of one embodiment of tissue anchor 1300. FIG. 5C shows another embodiment of tissue anchor 1300.

Tissue anchor 1300 may be configured to attach a device to a tissue wall. Tissue anchor 1300 may be configured to attach a cuff to a tissue wall.

Tissue anchor 1300 may include a first retention element 1310. First retention element 1310 may be configured to be placed on a first side of an anchoring membrane of a cuff. First retention element 1310 may be configured to be placed on a proximal side of an anchoring membrane of a cuff.

First retention element 1310 may include a T-tag 1311. T-tag 1311 may include a longitudinal cylindrical segment, such as one-third or one-fourth of a cylindrical tube cut lengthwise. T-tag 1311 may be configured to fit between the outside of a delivery needle and an inside of a catheter lumen. T-tag 1311 may be configured to fit in a gap between a delivery needle and a catheter lumen. T-tag 1311 may include a pull 1312 to facilitate removal. First retention element 1310 may include a button or other suitable device.

Tissue anchor 1300 includes a second retention element 1320. Second retention element 1320 may be configured to be placed on a second side of a tissue wall. Second retention element 1320 may be configured to be placed on a distal side of a tissue wall.

Second retention element 1320 may include a hub 1323. Hub 1323 may include a proximal portion 1323*p*, a distal portion 1323*d*, and a longitudinal axis 1323*a*.

Second retention element 1320 may include one or more petals 1324. Petals 1324 may be coupled to hub 1323. Petals 1324 may extend from distal portion 1323*d* of hub 1323. Petals 1324 may be configured to be collapsed inside a delivery needle. Petals 1324 may be coupled to hub 1323 by being at least partially inserted into opening 1324. Petals 1324 may be coupled to hub 1323 with any one or any combination of an adhesive, solder, weld, compression fit, and other suitable methods. Petals 1324 may be formed of lengths of wire. Hub 1323 and petals 1324 may be formed as one or more pieces.

Petals 1324 may include a contact portion 1325. Contact portion 1325 may be configured to be substantially perpendicular to longitudinal axis 1323*a* of hub 1323. Contact portion 1325 may be configured to be proximal to proximal portion 1323*p* of hub 1323.

Alternatively, second retention element 1320 may include a T-tag 1321, as shown in FIG. 5C. T-tag 1321 may be configured to be loaded in a delivery needle. Second retention element 1320 may include any of the second retention elements described in U.S. patent application publication nos. 2009/0012541 and 2015/0018745, which are incorporated by reference.

Tissue anchor 1300 includes a tension element 1350. Tension element 1350 may be configured to couple first retention element 1310 and second retention element 1320. Tension element 1350 may be configured to placed through an anchoring membrane and a tissue wall.

Tension element 1350 may include a suture 1351. Suture 1351 may have a proximal portion 1351*p* and a distal portion 1351*d*. Proximal portion 1351*p* of suture 1351 may be coupled to first retention element 1310. Proximal portion 1351*p* of suture 1351 may be coupled to T-tag 1311, such as with an adhesive and/or a knot. Distal portion 1351*d* of suture 1351 may be coupled to second retention element 1320. Distal portion 1351*d* of suture 1351 may be coupled to hub 1323 of second retention element 1320. Tension element 1350 may include a wire, a stent, or other suitable device. Tension element 1350 may be made of a polymer or other suitable material.

Alternatively, tissue anchor 1300 may include no first retention element 1310, and proximal portion 1351*p* of suture 1351 may be coupled to a cuff.

FIGS. 5D-5G show other embodiments of a tissue anchor 2300.

Tissue anchor 2300 may be configured to attach a device to a tissue wall. Tissue anchor 2300 may be configured to attach a cuff to a tissue wall.

Tissue anchor 2300 may include a first retention element 2310. First retention element 2310 may be configured to be placed on a first side of an anchoring membrane of a cuff. First retention element 2310 may be configured to be placed on a proximal side of an anchoring membrane of a cuff.

First retention element 2310 may include a hub 2313. Hub 2313 may include a proximal portion 2313*p*, a distal portion 2313*d*, and a longitudinal axis 2313*a*.

Figure 5D:
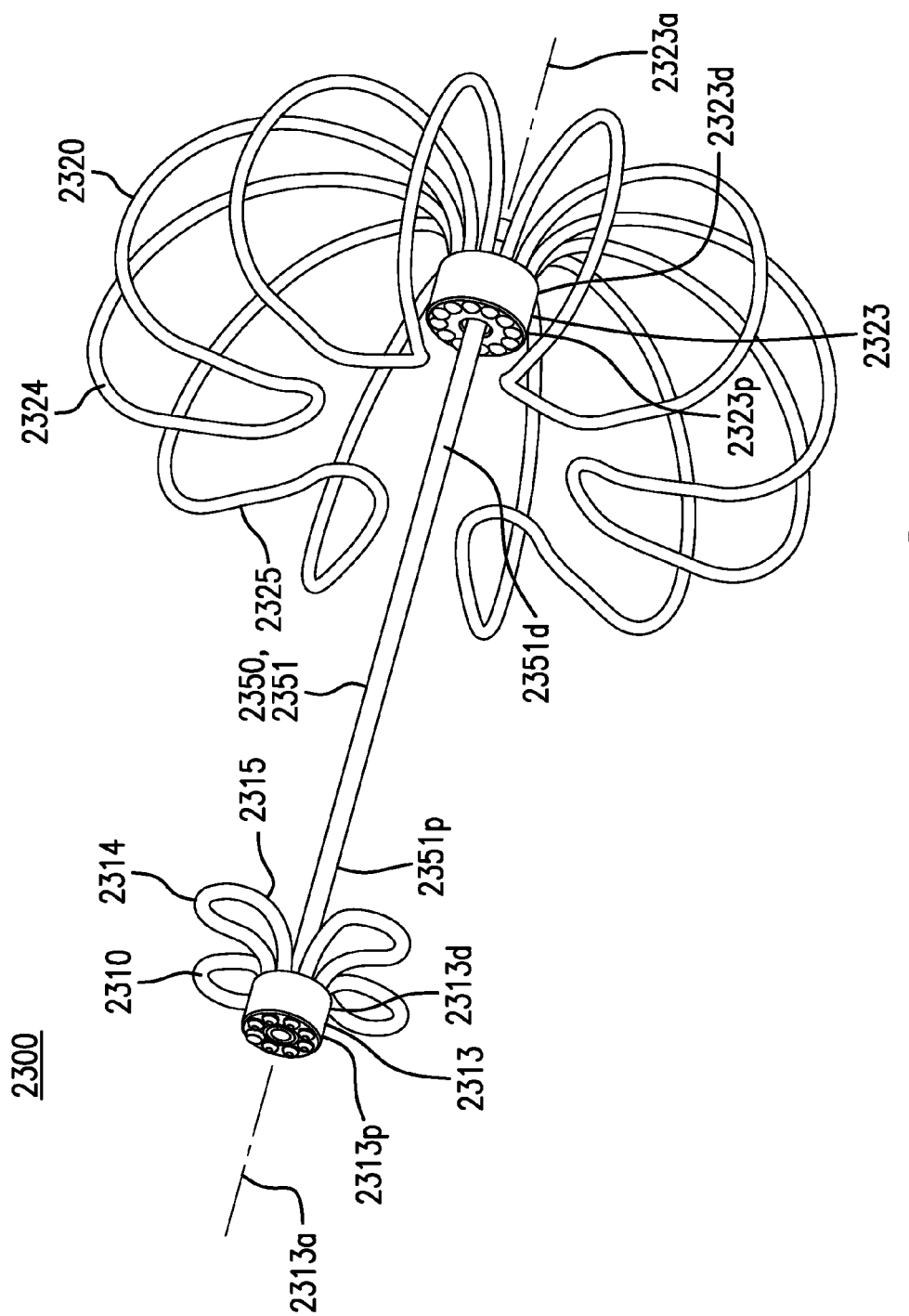
Figure 5E:
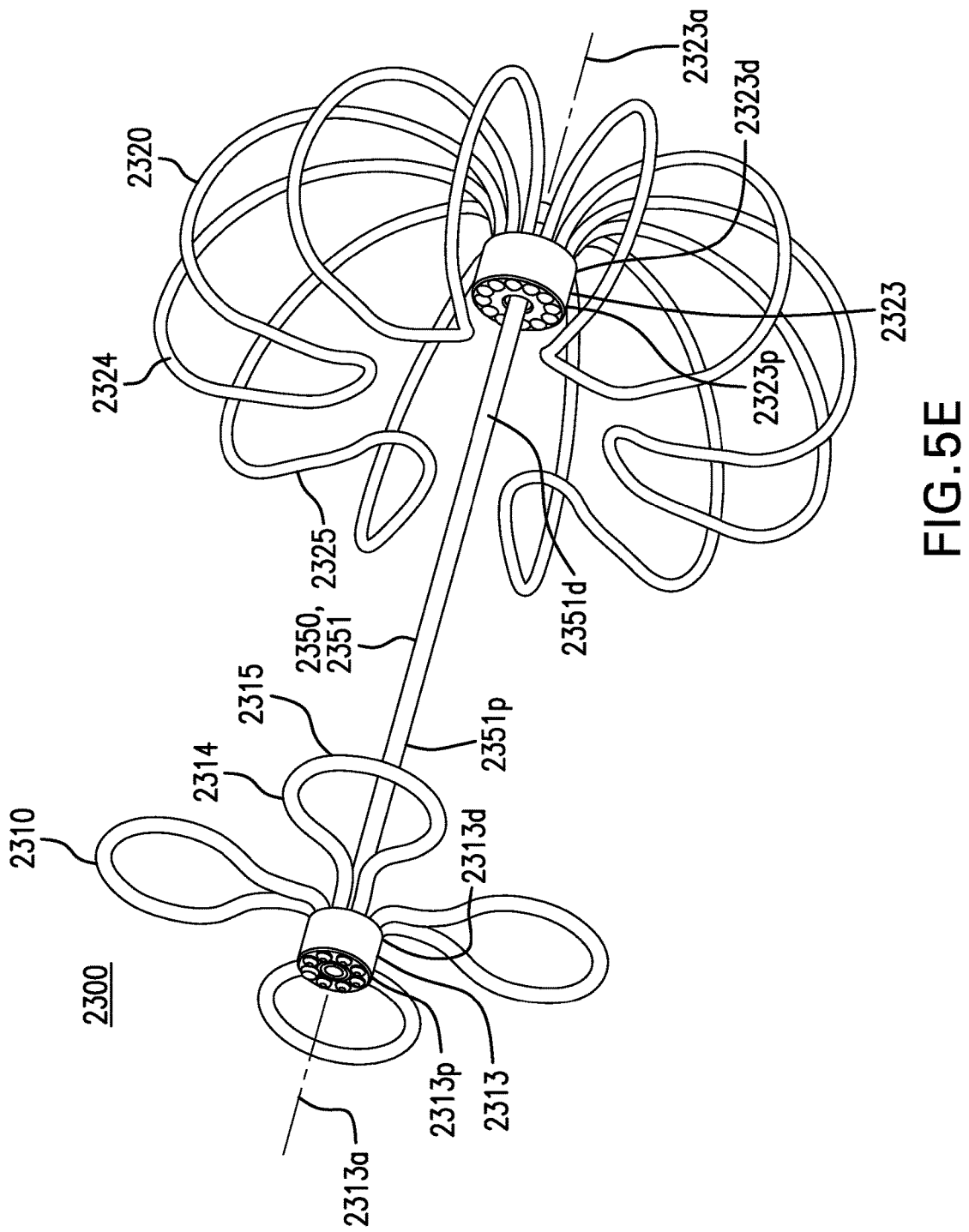
Figure 5G:
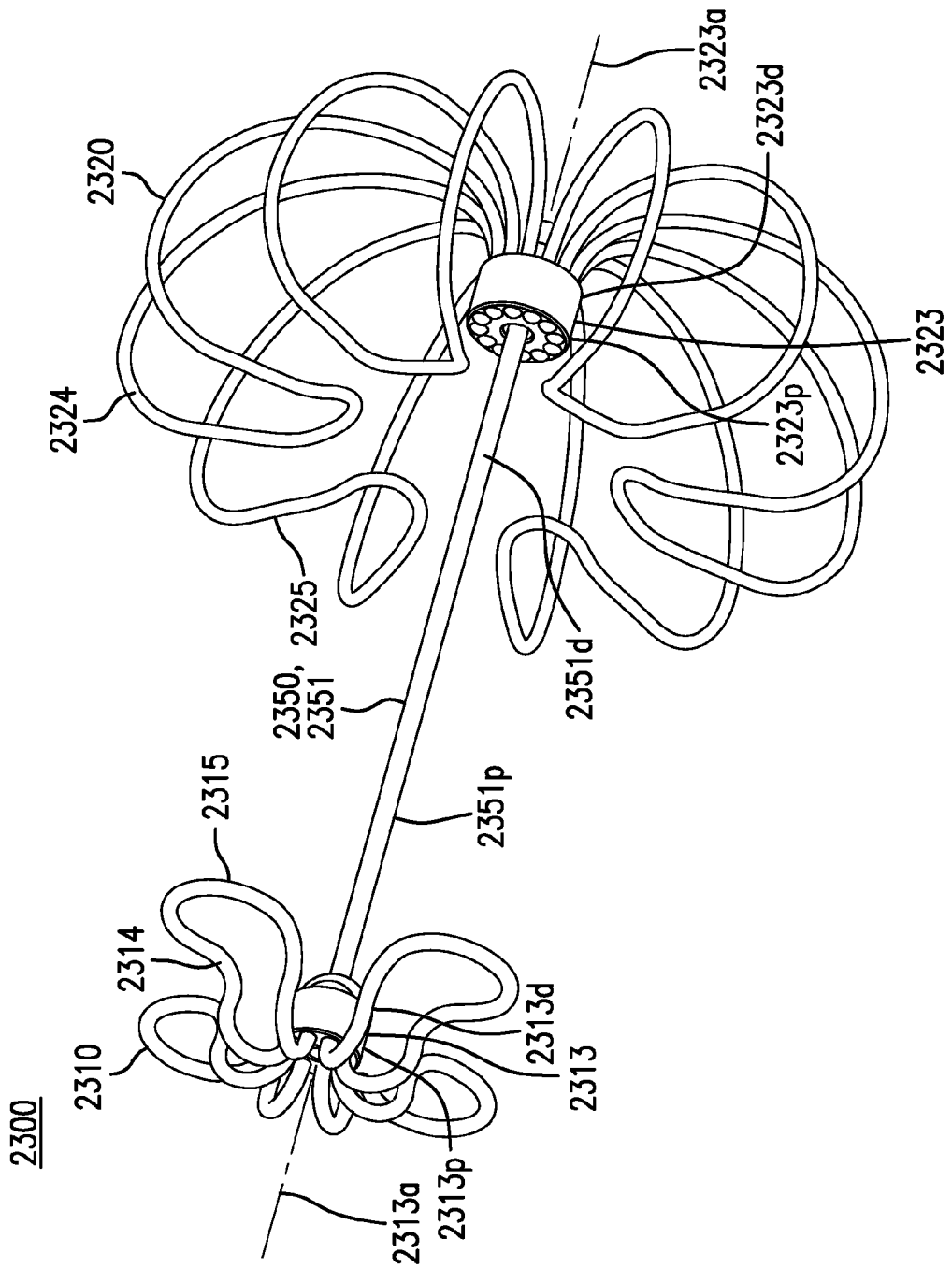

First retention element 2310 may include one or more petals 2314. Petals 2314 may be coupled to hub 2313. Petals 2314 may extend from distal portion 2313*d* of hub 2313, as shown in FIGS. 5D-5F. Petals 2314 may extend from proximal portion of hub 2313, as shown in FIG. 5G. Petals 2314 may be configured to be collapsed inside a delivery needle. Petals 2314 may be coupled to hub 2313 with any one or any combination of an adhesive, solder, weld, compression fit, and other suitable methods. Hub 2313 and petals 2314 may be formed as one piece, as shown in FIG. 5F. Hub 2313 and petals 2314 may be formed as two or more pieces, as shown in FIGS. 5D-5E and 5G.

Petals 2314 may include a contact portion 2315. Contact portion 2315 may be configured to be substantially perpendicular to longitudinal axis 2313*a* of hub 2313. Contact portion 2315 may be configured to be distal to distal portion 2313*d* of hub 2313.

Tissue anchor 2300 includes a second retention element 2320. Second retention element 2320 may be configured to be placed on a second side of a tissue wall. Second retention element 2320 may be configured to be placed on a distal side of a tissue wall.

Second retention element 2320 may include a hub 2323. Hub 2323 may include a proximal portion 2323*p*, a distal portion 2323*d*, and a longitudinal axis 2323*a*.

Second retention element 2320 may include one or more petals 2324. Petals 2324 may be coupled to hub 2323. Petals 2324 may extend from distal portion 2323*d* of hub 2323. Petals 2324 may be configured to be collapsed inside a delivery needle. Petals 2324 may be coupled to hub 2323 by being at least partially inserted into opening 2324. Petals 2324 may be coupled to hub 2323 with any one or any combination of an adhesive, solder, weld, compression fit, and other suitable methods. Petals 2324 may be formed of lengths of wire. Hub 2323 and petals 2324 may be formed as one or more pieces.

Petals 2324 may include a contact portion 2325. Contact portion 2325 may be configured to be substantially perpendicular to longitudinal axis 2323*a* of hub 2323. Contact portion 2325 may be configured to be proximal to proximal portion 2323*p* of hub 2323.

Alternatively, second retention element 2320 may include a T-tag. Second retention element 2320 may include any of the second retention elements described in U.S. patent application publication nos. 2009/0012541 and 2015/0018745, which are incorporated by reference.

Tissue anchor 2300 includes a tension element 2350. Tension element 2350 may be configured to couple first retention element 2310 and second retention element 2320. Tension element 2350 may be configured to placed through an anchoring membrane and a tissue wall.

Tension element 2350 may include a suture 2351. Suture 2351 may have a proximal portion 2351p and a distal portion 2351d. Proximal portion 2351p of suture 2351 may be coupled to first retention element 2310. Proximal portion 2351p of suture 2351 may be coupled to hub 2313 of first retention element 2310. Distal portion 2351d of suture 2351 may be coupled to second retention element 2320. Distal portion 2351d of suture 2351 may be coupled to hub 2323 of second retention element 2320. Tension element 2350 may include a wire, a stent, or other suitable device. Tension element 2350 may be made of a polymer or other suitable material.

Alternatively, tissue anchor 2300 may include no first retention element 2310, and proximal portion 2351p of suture 2351 may be coupled to a cuff.

Figure 5H:
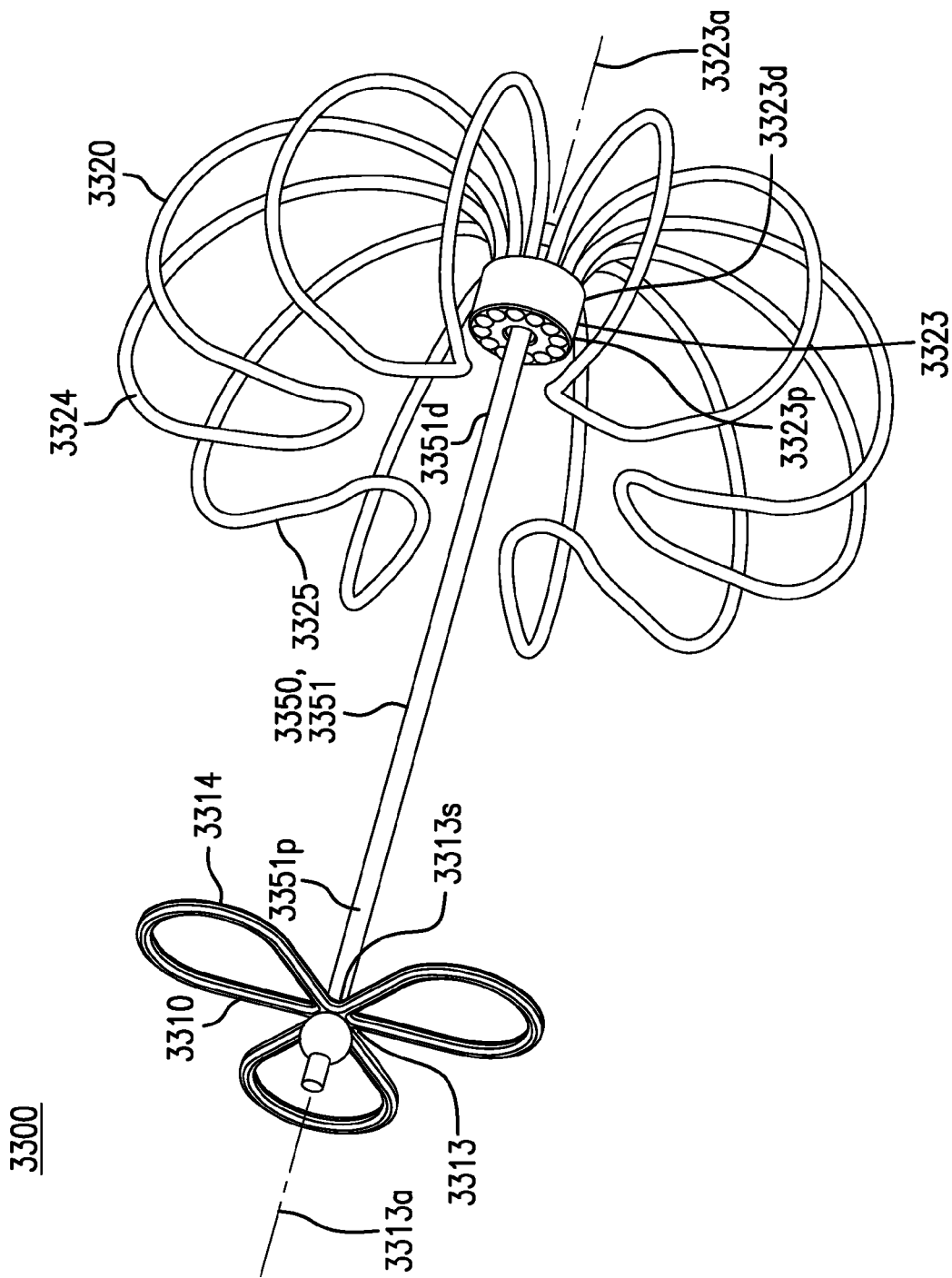
Figure 51:
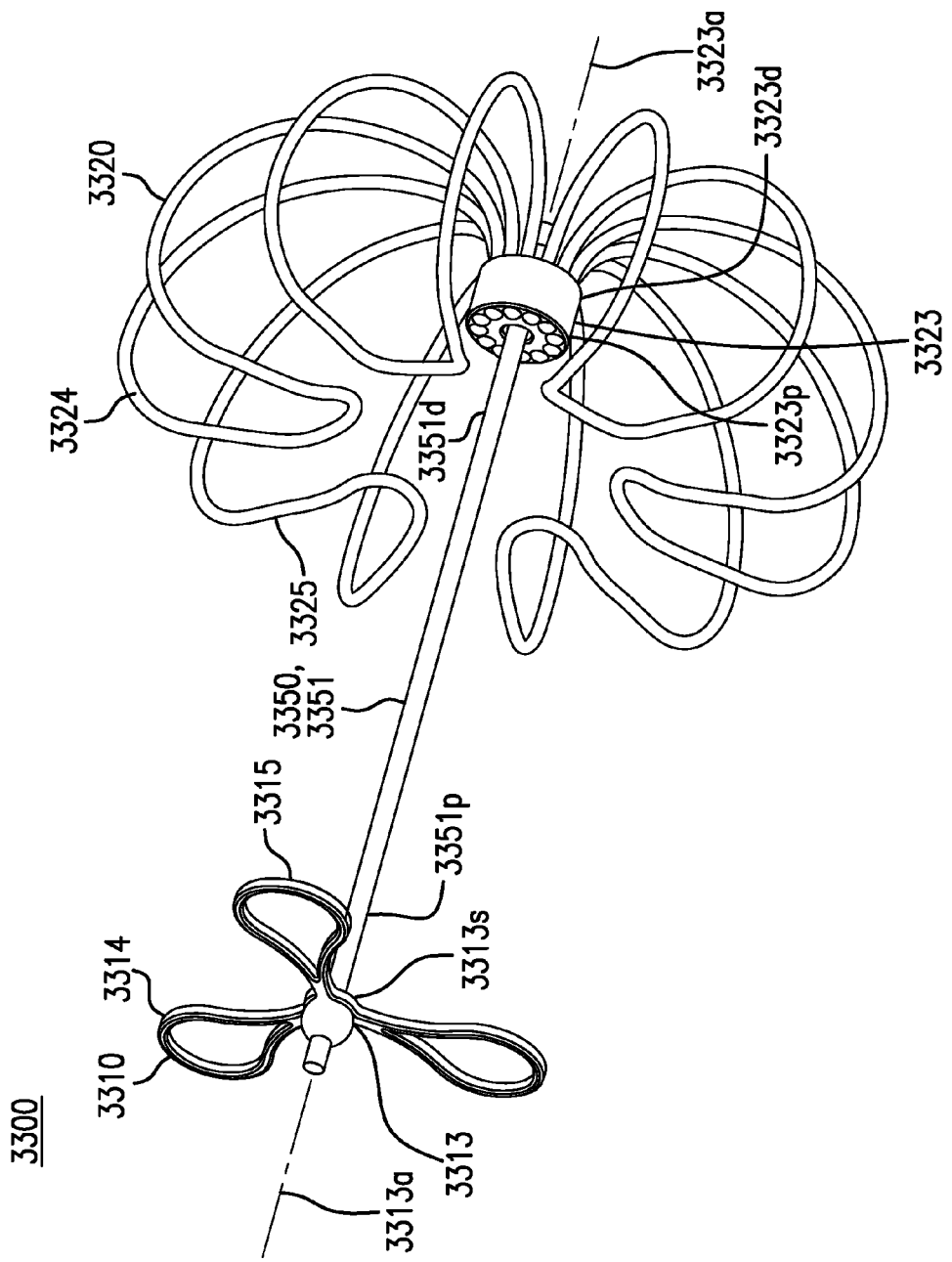

FIGS. 5H-5I show other embodiments of a tissue anchor 3300.

Tissue anchor 3300 may be configured to attach a device to a tissue wall. Tissue anchor 3300 may be configured to attach a cuff to a tissue wall.

Tissue anchor 3300 may include a first retention element 3310. First retention element 3310 may be configured to be placed on a first side of an anchoring membrane of a cuff. First retention element 3310 may be configured to be placed on a proximal side of an anchoring membrane of a cuff.

First retention element 3310 may include a hub 3313. Hub 3313 may include a side 3313s and a longitudinal axis 3313a.

First retention element 3310 may include one or more petals 3314. Petals 3314 may be coupled to hub 3313. Petals 3314 may extend from side 3313s of hub 3313. Petals 3314 may be configured to be collapsed inside a delivery needle. Petals 3314 may be coupled to hub 3313 with any one or any combination of an adhesive, solder, weld, compression fit, and other suitable methods. Hub 3313 and petals 3314 may be formed as one or more pieces.

Petals 3314 may include a contact portion 3315. Contact portion 3315 may be configured to be substantially perpendicular to longitudinal axis 3313a of hub 3313. Contact portion 3315 may be configured to be distal to distal portion 3313d of hub 3313.

Tissue anchor 3300 includes a second retention element 3320. Second retention element 3320 may be configured to be placed on a second side of a tissue wall. Second retention element 3320 may be configured to be placed on a distal side of a tissue wall.

Second retention element 3320 may include a hub 3323. Hub 3323 may include a proximal portion 3323p, a distal portion 3323d, and a longitudinal axis 3323a.

Second retention element 3320 may include one or more petals 3324. Petals 3324 may be coupled to hub 3323. Petals 3324 may extend from distal portion 3323d of hub 3323. Petals 3324 may be configured to be collapsed inside a delivery needle. Petals 3324 may be coupled to hub 3323 by being at least partially inserted into opening 3324. Petals 3324 may be coupled to hub 3323 with any one or any combination of an adhesive, solder, weld, compression fit, and other suitable methods. Petals 3324 may be formed of lengths of wire. Hub 3323 and petals 3324 may be formed as one or more pieces.

Petals 3324 may include a contact portion 3325. Contact portion 3325 may be configured to be substantially perpendicular to longitudinal axis 3323a of hub 3323. Contact portion 3325 may be configured to be proximal to proximal portion 3323p of hub 3323.

Alternatively, second retention element 3320 may include a T-tag. Second retention element 3320 may include any of the second retention elements described in U.S. patent application publication nos. 2009/0012541 and 2015/0018745, which are incorporated by reference.

Tissue anchor 3300 includes a tension element 3350. Tension element 3350 may be configured to couple first retention element 3310 and second retention element 3320. Tension element 3350 may be configured to placed through an anchoring membrane and a tissue wall.

Tension element 3350 may include a suture 3351. Suture 3351 may have a proximal portion 3351p and a distal portion 3351d. Proximal portion 3351p of suture 3351 may be coupled to first retention element 3310. Proximal portion 3351p of suture 3351 may be coupled to hub 3313 of first retention element 3310. Distal portion 3351d of suture 3351 may be coupled to second retention element 3320. Distal portion 3351d of suture 3351 may be coupled to hub 3323 of second retention element 3320. Tension element 3350 may include a wire, a stent, or other suitable device. Tension element 3350 may be made of a polymer or other suitable material.

Figure 6A:
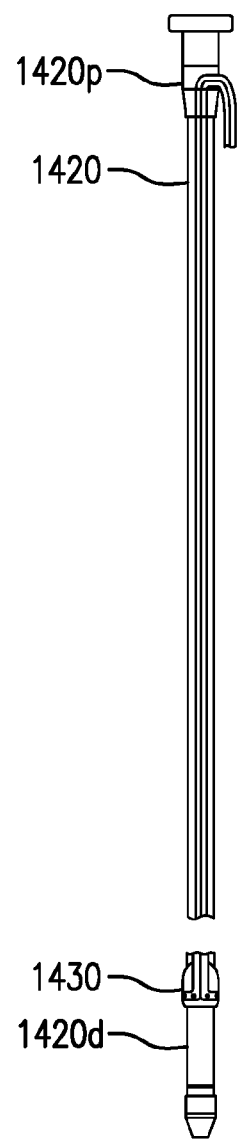
FIGS. 6A-6B show one embodiment of a tissue marking device 1400.
Figure 6B:
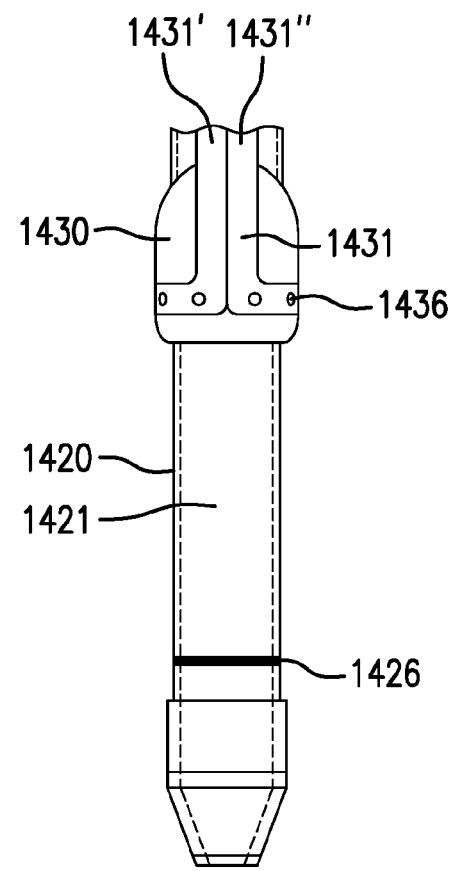

Alternatively, tissue anchor 3300 may include no first retention element 3310, and proximal portion 3351p of suture 3351 may be coupled to a cuff FIGS. 6A-6B show one embodiment of a tissue marking device 1400. FIG. 6A shows a side view of tissue marking device 1400. FIG. 6B shows an enlarged view of a marking surface 1420 of tissue marking device 1400.

Tissue marking device 1400 may be configured to mark a tissue wall. Tissue marking device 1400 may be configured to mark the esophagus, stomach, intestine, or any other part of the gastrointestinal tract.

Tissue marking device 1400 may include a catheter 1420. Catheter 1420 may include a proximal portion 1420p and a distal portion 1420d.

Catheter 1420 may include a primary lumen 1421. Primary lumen 1421 may be configured to accommodate an endoscope or other instrument.

Catheter 1420 may include at least one guide 1426. Guide 1426 may be at or near distal portion 1420d of catheter 1420. Guide 1426 may include a marking such as a line or other indicator. Guide 1426 may be configured to provide a reference to an anatomical landmark.

Tissue marking device 1400 may include a marking element 1430. Marking element 1430 may be formed on and/or coupled to an outside of catheter 1420. Alternatively, marking element 1430 may be coupled to an outside of an endoscope or other device.

Marking element 1430 may include a lumen 1431. Lumen 1431 may include an inlet 1431' and an outlet 1431". Inlet 1431' may be coupled to one or more sources of fluid. Fluids may include any one or any combination of a dye, a rinse fluid, a preparation fluid, and a therapeutic agent. Outlet 1431" may be coupled to a vacuum source.

Marking element 1430 may include a marking surface 1432. Marking surface 1432 may be configured to be positioned against a tissue wall to be marked. Marking surface 1432 may include one or more openings 1436. Openings 1436 may be in fluid communication with lumen 1431.

FIGS. 7A-7D show one embodiment of a method for marking tissue.

Figure 7A:
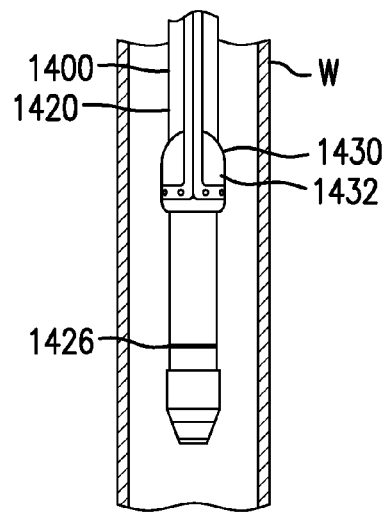
FIGS. 7A-7D show one embodiment of a method for marking tissue.

FIG. 7A shows positioning marking surface 1432 against a tissue wall W to be marked. Catheter 1420 of tissue marking device 1400 is advanced into the esophagus and marking surface 1432 of marking element 1430 is positioned against a tissue wall W to be marked. Guide 1426 may be positioned at an anatomical landmark such as the LES to facilitate positioning of marking surface 1432.

Figure 7B:
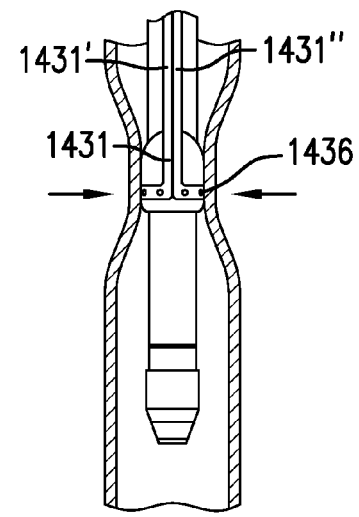

FIG. 7B shows drawing the tissue wall W into openings 1436 of marking surface 1432. Vacuum may be applied to lumen 1431 to draw the tissue wall W into openings 1436 of marking surface 1432. A seal may be formed between the tissue wall W and marking surface 1432. Inlet 1431' may be closed. Vacuum may be applied to outlet 1431". Alternatively, no vacuum may be used, and marking surface 1432 may be brought against the tissue wall W. Alternatively, catheter 1420 and/or marking surface 1432 may be sized so that the tissue wall W is brought against marking surface 1432.

Figure 7C:
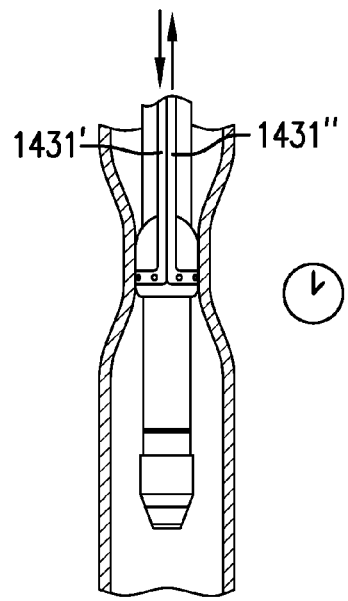

FIG. 7C shows marking the tissue wall W. A dye may be introduced into lumen 1431 through inlet 1431'. The dye comes into contact with portions of the tissue wall W that are drawn into openings 1436 of marking surface 1432. The dye may be maintained in lumen 1431 for a set period of time. The dye may be maintained in lumen 1431 by a vacuum applied to outlet 1431". The dye may be allowed to penetrate partially into or completely through the tissue wall W. The dye may then be removed.

Other fluids may be introduced into lumen 1431 through inlet 1431" and brought into contact with the tissue wall W. A rinse fluid may be used before and/or after the dye. A preparation fluid may be used before the dye. A therapeutic agent such as an antibiotic may be used. Each fluid may be removed first before another fluid is used.

Figure 7D:
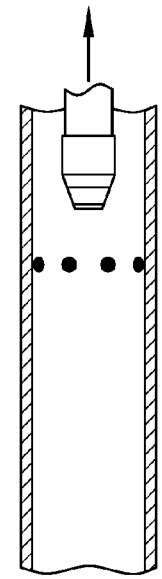

FIG. 7D shows withdrawing marking surface 1432. The vacuum applied to outlet 1431" is stopped. Catheter 1420 of tissue marking device 1400 is withdrawn from the tissue wall W.

Figure 8:
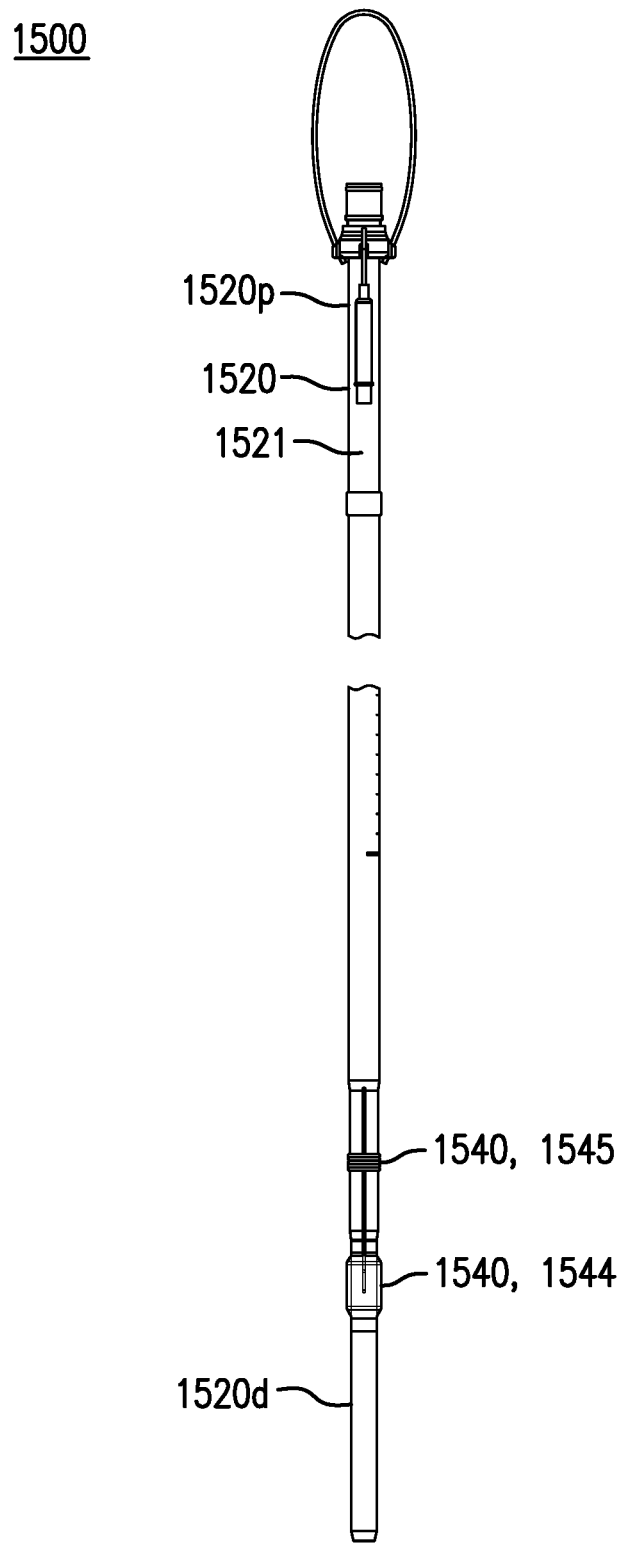
FIG. 8 shows one embodiment of a sleeve delivery device 1500.

FIG. 8 shows one embodiment of a sleeve delivery device 1500.

Sleeve delivery device 1500 may be configured to deliver a sleeve into the intestine.

Sleeve delivery device 1500 may include a catheter 1520. Catheter 1520 may include a proximal portion 1520p and a distal portion 1520d.

Catheter 1520 may include a primary lumen 1521. Primary lumen 1521 may be configured to accommodate an endoscope or other instrument.

Catheter 1520 may have a width of approximately 10 mm to 20 mm.

Sleeve delivery device 1500 may include one or more sealing elements 1540. Sealing elements 1540 may be formed on and/or coupled on an outside of catheter 1520. Sealing elements 1540 may be at or near distal portion 1520d of catheter 1520.

Sealing elements 1540 may be configured to form a seal with a cuff positioned over sealing elements 1540. Sealing elements 1540 may be configured to facilitate creating a seal between a cuff and catheter 1520. Sealing elements 1540 may be configured to facilitate creating a seal between an inside of a cuff and an outside of catheter 1520.

Sealing elements 1540 may include a balloon 1544. Balloon 1544 may be circumferential.

Balloon 1544 may be configured to be inflated inside a cuff positioned over balloon 1544 to form a seal.

Sealing elements 1540 may include at least one protrusion 1545. Protrusion 1545 may be proximal to balloon 1544. Protrusion 1545 may be circumferential. Protrusion 1545 may include any one or any combination of a ring, bump, and other suitable structure.

Protrusion 1545 may be configured to facilitate the cinching of a drawstring of a cuff at a position proximal to protrusion 1545 to prevent the cuff from sliding off distal portion 1520d of catheter 1520.

Figures 9A, 9B:
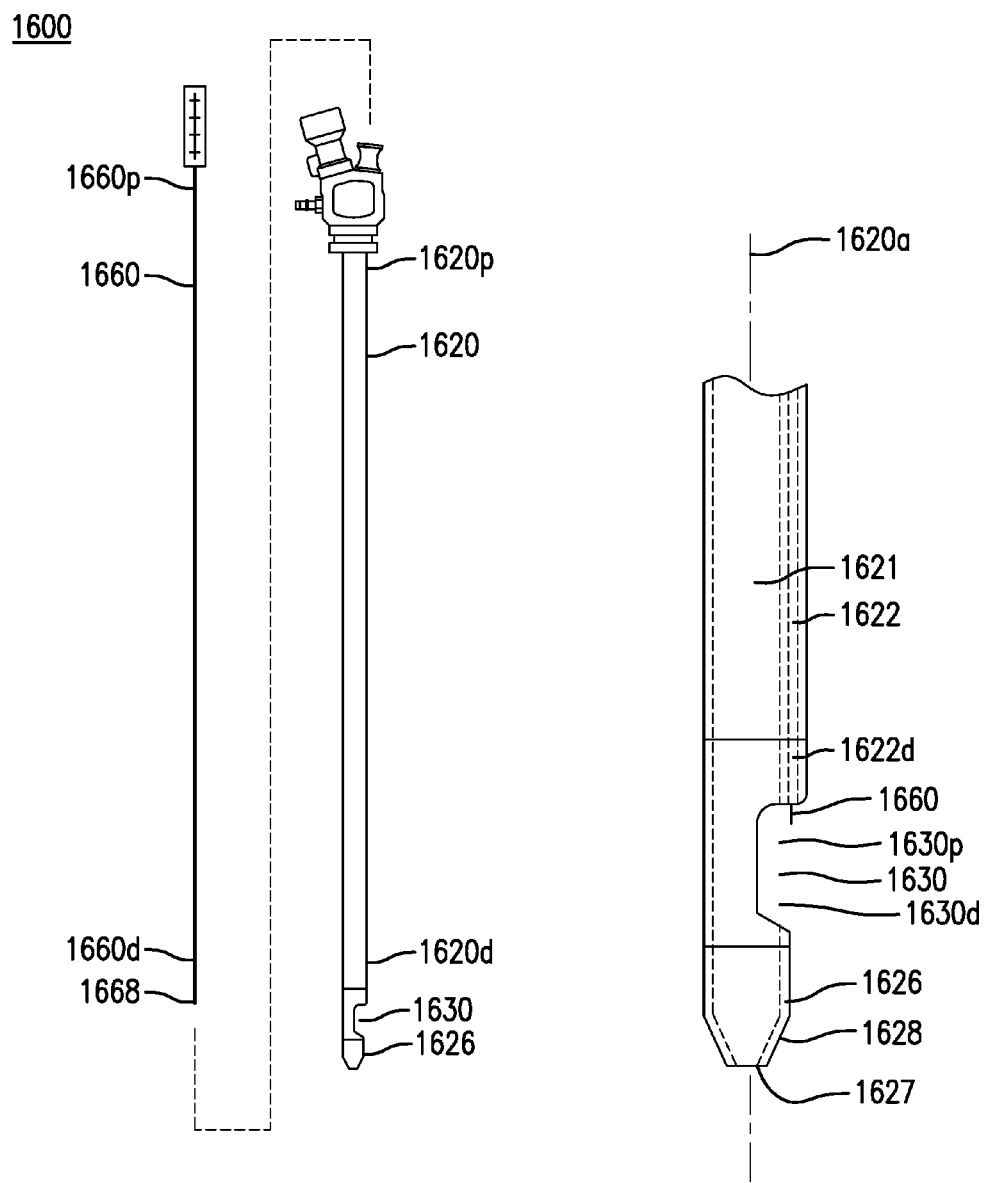
FIGS. 9A-9D show one embodiment of an anchor delivery device 1600.
Figure 9C:
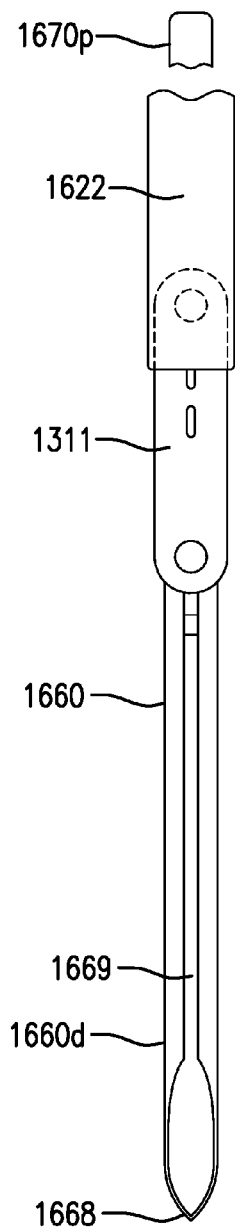
Figure 9D:
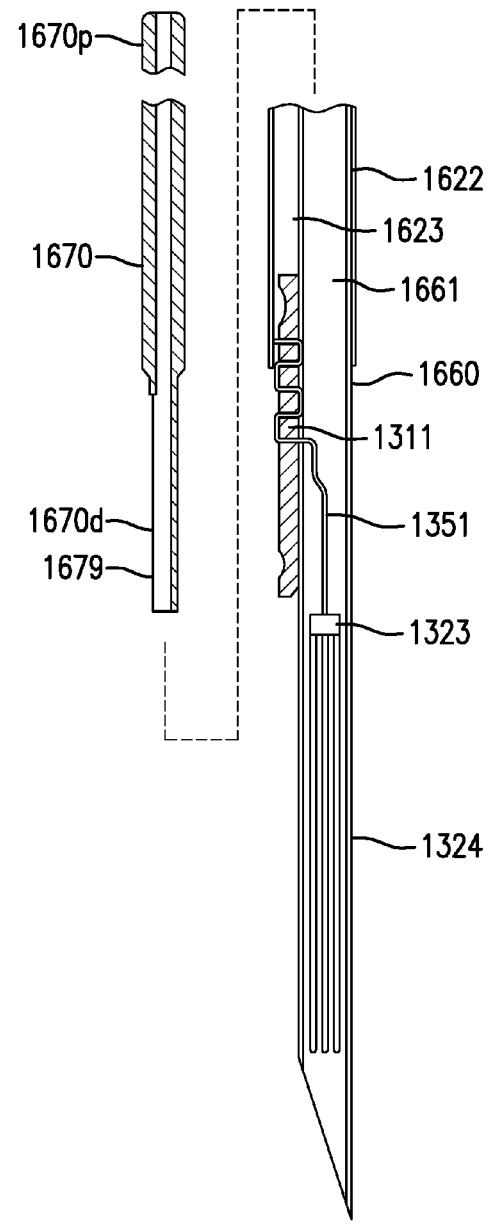

FIGS. 9A-9D show one embodiment of an anchor delivery device 1600. FIG. 9A shows a side view of anchor delivery device 1600. FIG. 9B shows an enlarged view of an anchoring cavity 1630 of anchor delivery device 1600. FIG. 9C shows an enlarged view of a delivery needle 1660. FIG. 9D shows a cross-sectional view of delivery needle 1660. FIGS. 9C-9D show delivery needle 1660 loaded with a tissue anchor 1300. FIGS. 9C-9D show delivery needle 1660 advanced out of a secondary lumen 1622 of a catheter 1620.

Anchor delivery device 1600 may be configured to place tissue anchors through a device and a tissue wall. Anchor delivery device 1600 may be configured to place tissue anchors through a cuff and a tissue wall.

Anchor delivery device 1600 may include a catheter 1620. Catheter 1620 may include a proximal portion 1620p, a distal portion 1620d, and a longitudinal axis 1620a.

Catheter 1620 may include a primary lumen 1621. Primary lumen 1621 may be configured to accommodate an endoscope or other instrument.

Catheter 1620 may include at least one secondary lumen 1622. Secondary lumen 1622 may be formed in a wall of catheter 1620. Secondary lumen 1622 may include a proximal portion 1622p and a distal portion 1622d. Secondary lumen 1622 may be configured to accommodate a delivery needle.

Distal portion 1622d of secondary lumen 1622 may be angled and/or curved inward toward longitudinal axis 1620a of catheter 1620. Distal portion 1622d of secondary lumen 1622 may be angled and/or curved inward toward longitudinal axis 1620a from approximately 0 degrees to 10 degrees.

Catheter 1620 may include a tip 1626. Tip 1626 may be coupled to distal portion 1620d of catheter 1620. Tip 1626 may include an opening 1627. Opening 1627 may be in communication with primary lumen 1621. Tip 1626 include a valve 1628 coupled to opening 1627. Valve 1628 may be configured to close opening 1627 when a vacuum is applied to primary lumen 1621. Valve 1628 may include a duckbill valve or any other suitable valve.

Catheter 1620 may have a width of approximately 10 mm to 20 mm.

Anchor delivery device 1600 may include an anchoring cavity 1630 formed in catheter 1620. Anchoring cavity 1630 may be formed in a side of catheter 1620. Anchoring cavity 1630 may be circumferential and extend completely around catheter 1620. Anchoring cavity 1630 may be formed at tip 1626 of catheter 1620. Anchoring cavity 1630 may include a proximal side 1630p and a distal side 1630d. Anchoring cavity 1630 may be at or near distal portion 1620d of catheter 1620. Anchoring cavity 1630 may be in communication with primary lumen 1621 and secondary lumen 1622.

Anchoring cavity 1630 may be configured to draw in a portion of an anchoring membrane. Anchoring cavity 1630 may be configured to draw in a portion of an anchoring membrane and a tissue wall.

Anchoring cavity 1630 may cut completely through distal portion 1622d of secondary lumen 1622. Distal portion 1622d of secondary lumen 1622 may be positioned at a proximal side 1630p of anchoring cavity 1630.

Anchoring cavity 1630 may have a length of approximately 10 mm to 40 mm. Anchoring cavity 1630 may have a width of approximately 10 mm to 20 mm.

Anchor delivery device 1600 may include a delivery needle 1660. Delivery needle 1660 may include a proximal portion 1660p and a distal portion 1660d. Delivery needle 1660 may be slidably disposed within secondary lumen 1622. Delivery needle 1660 may be configured to be advanced out of and withdrawn into secondary lumen 1622.

Delivery needle 1660 may include a needle lumen 1661. Needle lumen 1661 may be configured to be loaded with a second retention element of a tissue anchor in a collapsed or delivery configuration. Needle lumen 1661 may also be configured to be loaded with a first retention element and/or a second retention element of a tissue anchor in a collapsed or delivery configuration. Needle lumen 1661 may also be configured to be loaded with a therapeutic agent. Therapeutic agent may include any one or any combination of a phospholipid gel, hyaluronic acid, and other agents.

Delivery needle 1660 may include a tip 1668. Tip 1668 may be coupled to distal portion 1660d of delivery needle 1660. Tip 1668 may be configured to pierce an anchoring membrane. Tip 1668 may be configured to pierce a tissue wall. Tip 1668 may be sharp.

Delivery needle 1660 may include a slot 1669. Slot 1669 may be formed longitudinally at distal portion 1660d of delivery needle 1660. Slot 1669 may be configured to allow a tension element of a tissue anchor to pass through so that a second retention element of a tissue anchor may be loaded inside of needle lumen 1661 and a first retention element of a tissue element may be loaded outside of needle lumen 1661.

Distal portion 1660d of delivery needle 1660 may be angled and/or curved inward toward longitudinal axis 1620a of catheter 1620. Distal portion 1660d of delivery needle 1660 may be angled and/or curved inward toward longitudinal axis 1620a from approximately 0 degrees to 10 degrees. This may reduce the likelihood of contacting bodily parts on the other side of a tissue wall.

Delivery needle 1660 may be spring-loaded, and may be configured to be advanced out of and/or withdrawn into secondary lumen 1622 quickly, such as in 100 ms or less. This may reduce tenting of the tissue wall as delivery needle 1660 is advanced through the tissue wall.

Delivery needle 1660 and secondary lumen 1622 may be configured to define a gap 1623 when delivery needle 1660 is slidably disposed within secondary lumen 1622. Delivery needle 1660 and secondary lumen 1622 may have sizes selected to define a gap 1623 when delivery needle 1660 is slidably disposed within secondary lumen 1622. Gap 1623 may be configured to be loaded with a proximal delivery element of a tissue anchor. Gap 1623 may be configured to be loaded with a proximal delivery element such as a T-tag that is thin and elongate. Gap 1623 may be configured to be loaded with proximal delivery element such as a T-tag such as T-tag 1311 of tissue anchor 1300.

Anchor delivery device 1600 may include a pushrod 1670. Pushrod 1670 may include a proximal portion 1670p and a distal portion 1670d. Pushrod 1670 may be slidably disposed within needle lumen 1661.

Pushrod 1670 may be configured to push a second retention element of a tissue anchor out of needle lumen 1661 of delivery needle 1660. Pushrod 1670 may be configured to push a first retention element of a tissue anchor out of needle lumen 1661.

Pushrod 1670 may include a channel 1679. Channel 1679 may be formed longitudinally at distal portion 1670d of pushrod 1670. Channel 1679 may be configured to allow a tension element of a tissue anchor to pass through. Channel 1679 may be aligned with slot 1669 of delivery needle 1660.

Figure 10E:
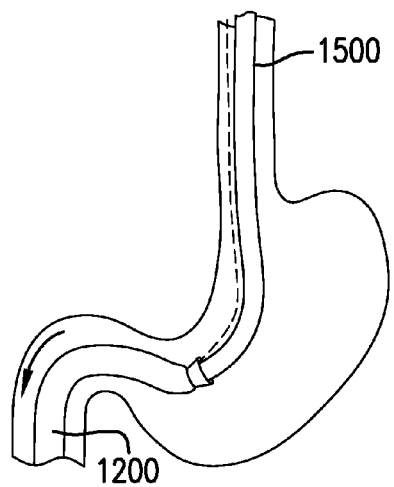
FIGS. 10A-10N show one embodiment of a method for delivering a gastrointestinal bypass device.
Figure 10F:
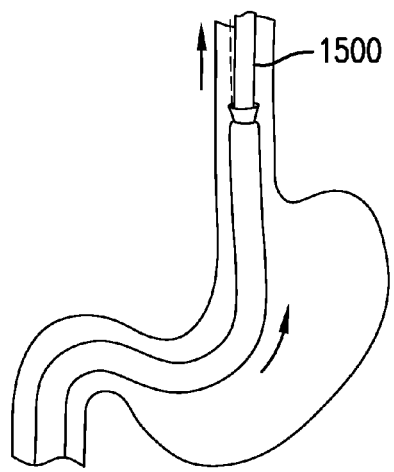
Figure 10G:
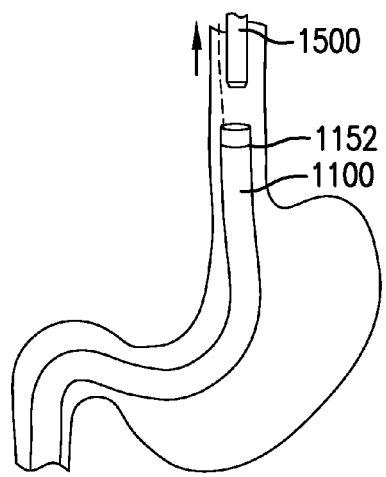
Figure 10H:
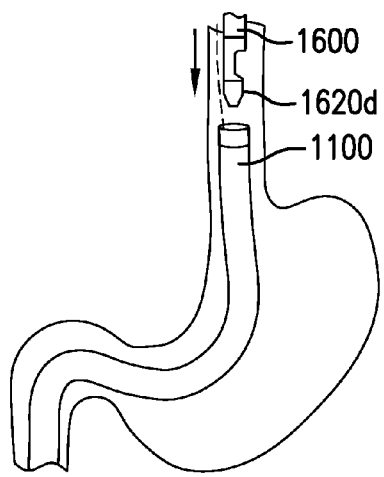
Figure 10I:
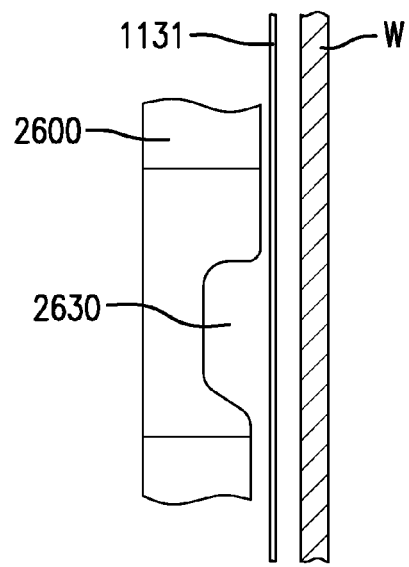
Figure 10J:
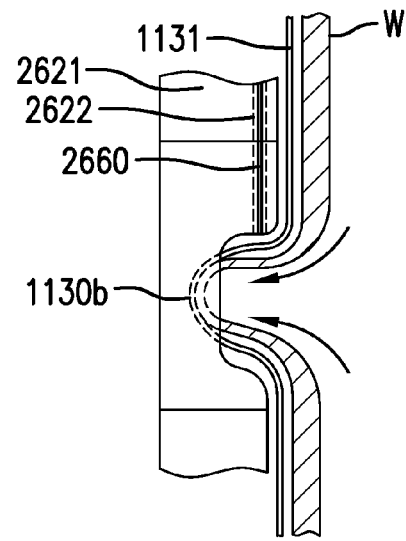
Figure 10K:
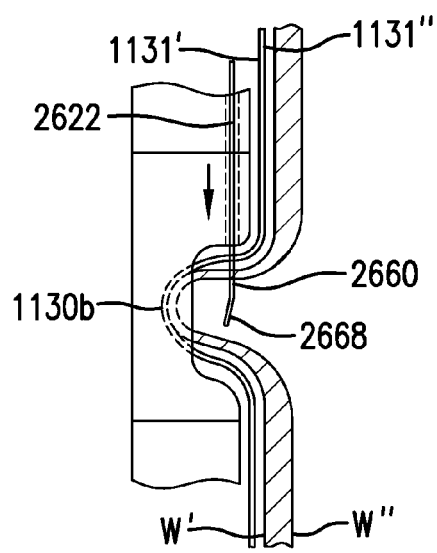
Figure 10L:
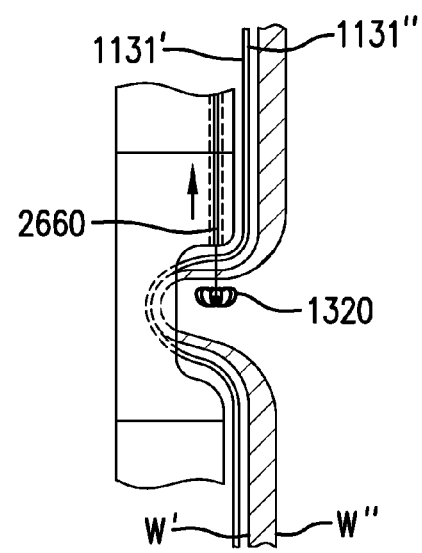
Figure 10M:
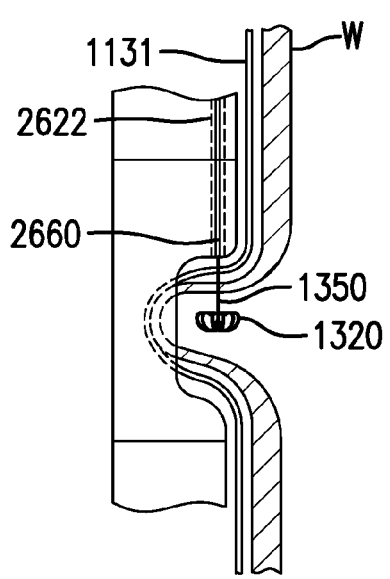
Figure 10N:
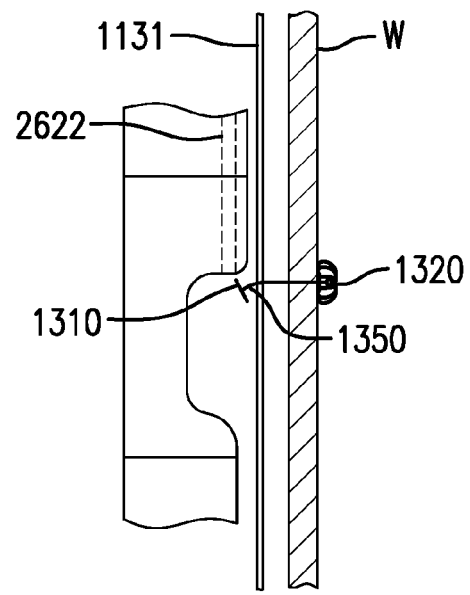

FIGS. 10A-10N show one embodiment of a method for delivering a gastrointestinal bypass device. Although delivery of gastrointestinal bypass device 1000 is shown as an example, the method may also be used to deliver other gastrointestinal bypass devices, such as gastrointestinal bypass devices 2000, 3000, and 4000.

FIG. 10A shows loading cuff 1100 onto sleeve delivery device 1500. Distal portion 1520d of catheter 1520 may be inserted into the lumen of cuff 1100. Protrusion 1545 may be positioned distal of drawstring 1152 of cuff 1100.

FIG. 10B shows forming a seal between sleeve delivery device 1500 and cuff 1100. Drawstring 1152 may be cinched proximal to protrusion 1545 to form a seal between sleeve delivery device 1500 and cuff 1100. Balloon 1544 may be inflated to form a seal between sleeve delivery device 1500 and cuff 1100.

FIG. 10C shows inverting sleeve 1200 into primary lumen 1521 of catheter 1520. A loop snare may be inserted through proximal portion 1520p of catheter 1520 into primary lumen 1521. The loop snare may pass through sleeve 1200 and be coupled to distal portion 1250d of tube 1250. The loop snare may pull distal portion 1250d of tube 1250 into primary lumen 1521 to invert sleeve 1200 into primary lumen 1521.

FIG. 10D shows positioning distal portion 1520d of catheter 1520 at or near the pylorus P. Catheter 1520 is advanced through the esophagus E and stomach S until distal portion 1520d of catheter 1520 is positioned at or near the pylorus P. An endoscope may be used in primary lumen 1521 inside inverted sleeve 1200 to guide catheter 1520. A tether T may be used to adjust the position of cuff 1100 and/or control drawstring 1152.

FIG. 10E shows everting sleeve 1200 into the intestine. The endoscope may be removed from primary lumen 1521 of catheter 1520. Distal portion 1250d of tube 1250 may be temporarily closed with a loop snare. Fluid may be pumped through primary lumen 1521 to evert sleeve 1200 into the intestine. Distal portion 1250d of tube 1250 may then be opened.

FIG. 10F shows positioning cuff 1100 at an attachment point. Catheter 1520 may be moved proximally to position anchoring membrane 1131 of cuff 1100 at an attachment point in the esophagus E. Tissue marks made previously by tissue marking device 1400 may be used as a guide.

The attachment point may be approximately 5 mm to 25 mm above the opening of the stomach. The attachment point may be approximately 0 mm to 20 mm above the squamocolumnar junction (SCJ). The attachment point may be approximately 20 mm below to 50 mm above the diaphragm. The attachment point may be a proximal portion of the LES.

FIG. 10G shows releasing the seal between sleeve delivery device 1500 and cuff 1100. Drawstring 1152 may be uncinched to release the seal between sleeve delivery device 1500 and cuff 1100. Balloon 1544 may be deflated to release the seal between sleeve delivery device 1500 and cuff 1100. Sleeve delivery device 1500 may then be withdrawn from the esophagus E.

FIG. 10H shows introducing anchor delivery device 1600 into the lumen of cuff 1100. Distal portion 1620d of catheter 1620 is advanced into the esophagus and into the lumen of cuff 1100. An endoscope may be used in primary lumen 1621 of catheter 1620 to guide catheter 1620 and visualize anchoring cavity 1630. Drawstring 1152 may be used to prevent cuff 1100 from traveling distally.

FIG. 10I shows positioning anchoring cavity 1630 of anchor delivery device 1600 next to anchoring membrane 1131 and the tissue wall W.

FIG. 10J shows forming a bulge 1130b in anchoring membrane 1131 and the tissue wall W. Delivery needle 1660 is retracted completely within secondary lumen 1622. A vacuum may be applied to anchoring cavity 1630 to draw anchoring membrane 1131 and the tissue wall W into anchoring cavity 1630 to form bulge 1130*b*. The vacuum may be approximately 50 mmHg to 500 mmHg.

Alternatively, anchoring membrane 1131 and the tissue wall W may be pulled into anchoring cavity 1630 by a grasper or other suitable device to form bulge 1130*b*. Alternatively, anchoring membrane 1131 and the tissue wall W may be allowed to enter anchoring cavity 1630 without assistance, such as from muscle activity of the tissue wall W, to form bulge 1130*b*.

FIG. 10K shows piercing bulge 1130*b* from a first side 1131' of anchoring membrane 1131 and a first side W' of the tissue wall W. Delivery needle 1660 may be advanced a set distance out of secondary lumen 1622 of catheter 1620. Delivery needle 1660 may be advanced through bulge 1130*b* to position tip 1668 of delivery needle 1660 on a second side W" of the tissue wall W.

Delivery needle 1660 may be advanced in a direction substantially parallel to longitudinal axis 1620*a* of catheter. Delivery needle 1660 may be advanced in a direction substantially parallel to the tissue wall W other than bulge 1130*b*. Delivery needle 1660 may be advanced in a direction approximately 0 degrees to 10 degrees from parallel toward longitudinal axis 1620*a* of catheter. Delivery needle 1660 may be advanced in a direction approximately 0 degrees to 10 degrees from parallel away from the tissue wall W other than bulge 1130*b*.

FIG. 10L shows placing second retention element 1320 of tissue anchor 1300 on a second side W" of the tissue wall W. Delivery needle 1660 may be pulled back over pushrod 1670 to release second retention element 1320 from needle lumen 1661. Alternatively, pushrod 1670 may be advanced a set distance through delivery needle 1660 to release second retention element 1320 from needle lumen 1661. A therapeutic agent may also be released from needle lumen 1661. Second retention element 1320 expands.

FIG. 10M shows placing tension element 1350 of tissue anchor 1300 through anchoring membrane 1131 and the tissue wall W. Delivery needle 1660 and pushrod 1670 may be pulled back through the tissue wall W and pulled back through anchoring membrane 1131 to place tension element 1350 through the tissue wall W and anchoring membrane 1131.

Delivery needle 1660 may be spring-loaded, so that any combination of the steps shown in FIGS. 10K-10M may be performed quickly, such as in 100 ms or less.

FIG. 10N shows placing first retention element 1310 of tissue anchor 1300 on first side 1131' of anchoring membrane 1131. Bulge 1130*b* may be released. Vacuum applied to anchoring cavity 1630 may be stopped. First retention element 1310 is placed on first side 1131' of anchoring membrane 1131. First retention element 1310 may be pulled out of secondary lumen 1622 of catheter 1620 by tension element 1350.

Alternatively, delivery needle 1660 may be advanced through bulge 1130*b* at both proximal side 1630*p* and distal side 1630*d* of anchoring cavity 1630, to position tip 1668 of delivery needle 1660 back on first side 1131' of anchoring membrane 1131. Second retention element 1320 may be placed on first side 1131' of anchoring membrane 1131, tension element 1350 may be placed through anchoring membrane 1131 and the tissue wall W at two points, and first retention element 1310 may also be placed on first side 1131' of anchoring membrane 1131.

Alternatively, delivery needle 1660 may be advanced only partially through bulge 1130*b* at proximal side 1630*p* of anchoring cavity 1630. Delivery needle 1660 may be advanced through anchoring membrane 1131 and only partially through the tissue wall W, to position tip 1668 of delivery needle 1660 within the tissue wall W, such as between layers of the tissue wall W. Second retention element 1320 may be placed within the tissue wall W, tension element 1350 may be placed through anchoring membrane 1131 and part of the thickness of tissue wall W, and first retention element 1310 may be placed on first side 1131' of anchoring membrane 1131.

Anchor delivery device 1600 may be rotated within cuff 1100 to deliver one or more additional tissue anchors. Delivery needle 1660 may be removed from secondary lumen 1622 to be reloaded with another tissue anchor, or exchanged for another delivery needle 1660 that has already been loaded.

Figure 11A:
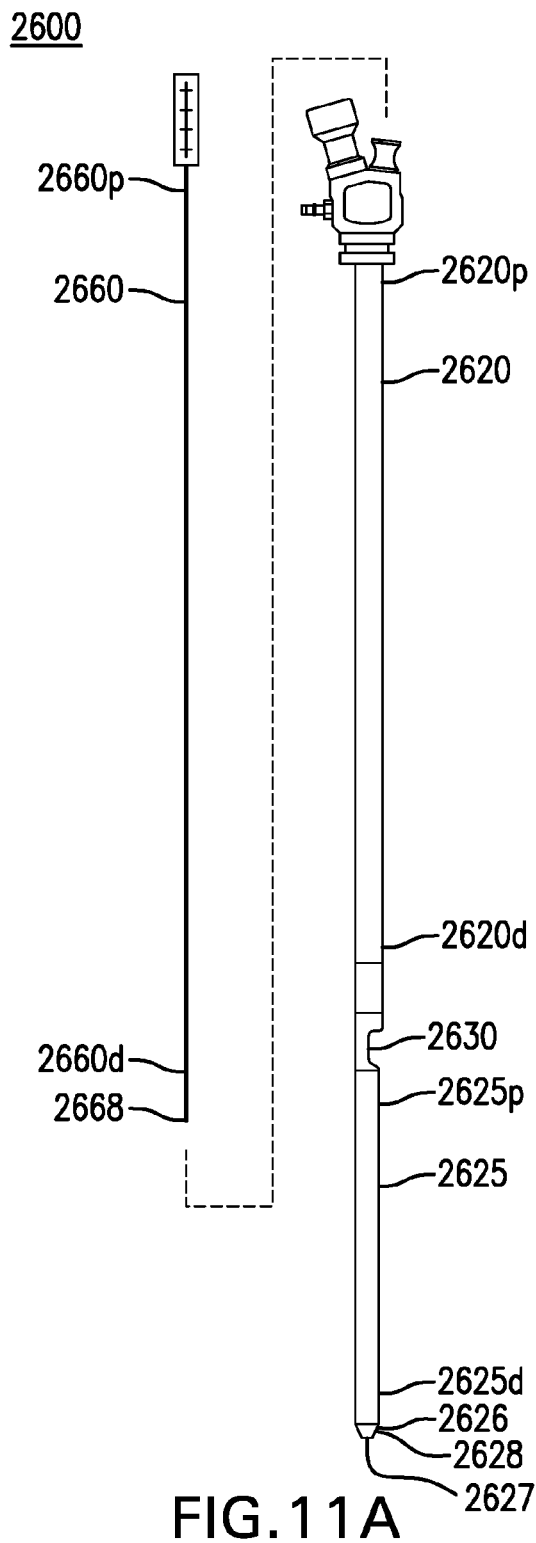
FIGS. 11A-11D show one embodiment of a combined delivery device 2600.
Figure 11B:
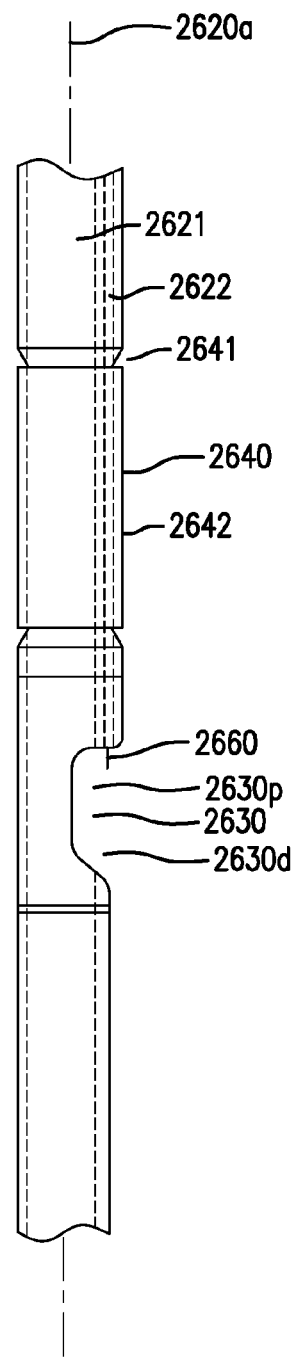
Figure 11C:
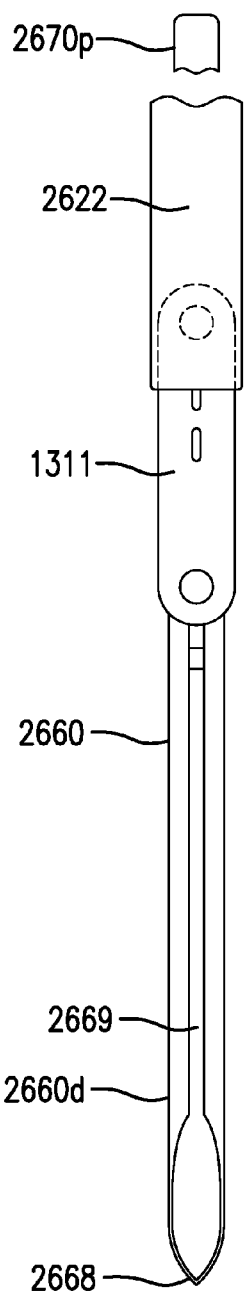
Figure 11D:
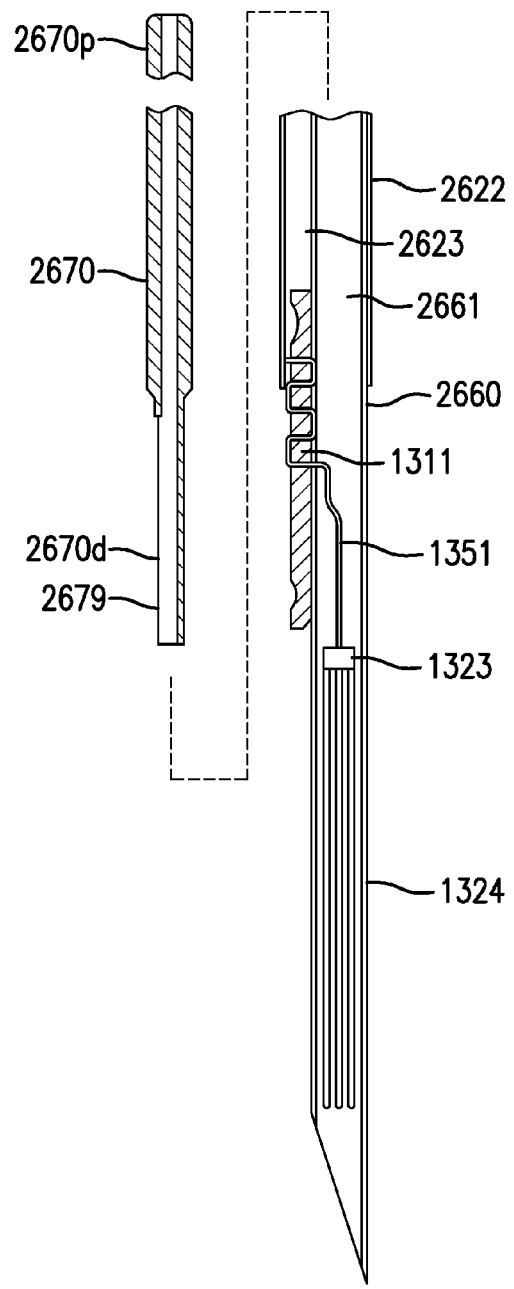

FIGS. 11A-11C show one embodiment of a combined delivery device 2600. FIG. 11A shows a side view of combined delivery device 2600. FIG. 11B shows an enlarged view of an anchoring cavity 2630 of combined delivery device 2600. FIG. 11C shows an enlarged view of a delivery needle 2660. FIG. 11D shows a cross-sectional view of delivery needle 2660. FIGS. 11C-11D show delivery needle 2660 loaded with a tissue anchor 1300. FIGS. 11C-11D show delivery needle 2660 advanced out of a secondary lumen 2622 of a catheter 2620.

Combined delivery device 2600 may be configured to deliver a sleeve in the intestine. Combined delivery device 2600 may be configured to place tissue anchors through a device and a tissue wall. Combined delivery device 2600 may be configured to place tissue anchors through a cuff and a tissue wall.

Combined delivery device 2600 may include a catheter 2620. Catheter 2620 may include a proximal portion 2620*p*, a distal portion 2620*d*, and a longitudinal axis 2620*a*.

Catheter 2620 may include a primary lumen 2621. Primary lumen 2621 may be configured to accommodate an endoscope or other instrument.

Catheter 2620 may include at least one secondary lumen 2622. Secondary lumen 2622 may be formed in a wall of catheter 2620. Secondary lumen 2622 may include a proximal portion 2622*p* and a distal portion 2622*d*. Secondary lumen 2622 may be configured to accommodate a delivery needle.

Distal portion 2622*d* of secondary lumen 2622 may be angled and/or curved inward toward longitudinal axis 2620*a* of catheter 2620. Distal portion 2622*d* of secondary lumen 2622 may be angled and/or curved inward toward longitudinal axis 2620*a* from approximately 0 degrees to 10 degrees.

Catheter 2620 may include an extension 2625. Extension 2625 may include a proximal portion 2625*p* and a distal portion 2625*d*. Proximal portion 2625*p* of extension 2625 may be coupled to distal portion 2620*d* of catheter 2620. Primary lumen 2621 may extend through extension 2625.

Extension 2625 may be flexible. Extension 2625 may be configured to be bendable. Extension 2625 may be configured to hold a shape into which it is bent.

Catheter 2620 may include a tip 2626. Tip 2626 may be coupled to distal portion 2625*d* of extension 2625. Tip 2626 may include an opening 2627. Opening 2627 may be in communication with primary lumen 2621. Tip 2626 include a valve 2628 coupled to opening 2627. Valve 2628 may be configured to close opening 2627 when a vacuum is applied to primary lumen 1621. Valve 2628 may include a duckbill valve or any other suitable valve.

Catheter 2620 may have a width of approximately 10 mm to 20 mm.

Combined delivery device 2600 may include an anchoring cavity 2630 formed in catheter 2620. Anchoring cavity 2630 may be formed in a side of catheter 2620. Anchoring cavity 2630 may be circumferential and extend completely around catheter 2620. Anchoring cavity 2630 may be formed at tip 2626 of catheter 2620. Anchoring cavity 2630 may include a proximal side 2630p and a distal side 2630d. Anchoring cavity 2630 may be at or near distal portion 2620d of catheter 2620. Anchoring cavity 2630 may be in communication with primary lumen 2621 and secondary lumen 2622.

Anchoring cavity 2630 may be configured to draw in a portion of an anchoring membrane. Anchoring cavity 2630 may be configured to draw in a portion of an anchoring membrane and a tissue wall.

Anchoring cavity 2630 may cut completely through distal portion 2622d of secondary lumen 2622. Distal portion 2622d of secondary lumen 2622 may be positioned at a proximal side 2630p of anchoring cavity 2630.

Anchoring cavity 2630 may have a length of approximately 10 mm to 40 mm. Anchoring cavity 2630 may have a width of approximately 10 mm to 20 mm.

Combined delivery device 2600 may include a sealing element 2640. Sealing element 2640 may be formed and/or coupled to an outside of catheter 2620. Sealing element 2640 may be proximal to anchoring cavity 2630.

Sealing element 2640 may be configured to form a seal with a cuff positioned over sealing element 2640. Sealing element 2640 may be configured to facilitate creating a seal between a cuff and catheter 2620. Sealing element 2640 may be configured to facilitate creating a seal between an inside of a cuff and an outside of catheter 2620.

Sealing element 2640 may include a recess 2641. Recess 2641 may be formed in an outside surface of catheter 2620. Recess 2641 may be circumferential in an outside surface of catheter 2620. Recess 2641 may be shorter than a cuff.

Recess 2641 may be configured to facilitate cinching of a drawstring of a cuff into catheter 2620 at recess 2641 to prevent the cuff from sliding off distal portion 2620d of catheter 2620.

Sealing element 2640 may include a sealing pad 2642. Sealing pad 2642 may be circumferential around catheter 2620. Sealing pad 2642 may be coupled to catheter 2620 with an adhesive and/or a compression fit. Sealing pad 2642 may be coupled at least partly within recess 2641.

Sealing pad 2642 may be configured to facilitate cinching of a drawstring of a cuff into catheter 2620 at sealing pad 2642 to form a seal.

Sealing pad 2642 may be made of a soft material. Sealing pad 2642 may be made of silicone or other suitable material.

Combined delivery device 2600 may include a delivery needle 2660. Delivery needle 2660 may include a proximal portion 2660p and a distal portion 2660d. Delivery needle 2660 may be slidably disposed within secondary lumen 2622. Delivery needle 2660 may be configured to be advanced out of and withdrawn into secondary lumen 2622.

Delivery needle 2660 may include a needle lumen 2661. Needle lumen 2661 may be configured to be loaded with a second retention element of a tissue anchor in a collapsed or delivery configuration. Needle lumen 2661 may also be configured to be loaded with a first retention element and/or a second retention element of a tissue anchor in a collapsed or delivery configuration. Needle lumen 2661 may also be configured to be loaded with a therapeutic agent. Therapeutic agent may include any one or any combination of a phospholipid gel, hyaluronic acid, and other agents.

Delivery needle 2660 may include a tip 2668. Tip 2668 may be coupled to distal portion 2660d of delivery needle 2660. Tip 2668 may be configured to pierce an anchoring membrane. Tip 2668 may be configured to pierce a tissue wall. Tip 2668 may be sharp.

Delivery needle 2660 may include a slot 2669. Slot 2669 may be formed longitudinally at distal portion 2660d of delivery needle 2660. Slot 2669 may be configured to allow a tension element of a tissue anchor to pass through so that a second retention element of a tissue anchor may be loaded inside of needle lumen 2661 and a first retention element of a tissue element may be loaded outside of needle lumen 2661.

Distal portion 2660d of delivery needle 2660 may be angled and/or curved inward toward longitudinal axis 2620a of catheter 2620. Distal portion 2660d of delivery needle 2660 may be angled and/or curved inward toward longitudinal axis 2620a from approximately 0 degrees to 10 degrees. This may reduce the likelihood of contacting bodily parts on the other side of a tissue wall.

Delivery needle 2660 may be spring-loaded, and may be configured to be advanced out of and/or withdrawn into secondary lumen 2622 quickly, such as in 100 ms or less. This may reduce tenting of the tissue wall as delivery needle 2660 is advanced through the tissue wall.

Delivery needle 2660 and secondary lumen 2622 may be configured to define a gap 2623 when delivery needle 2660 is slidably disposed within secondary lumen 2622. Delivery needle 2660 and secondary lumen 2622 may have sizes selected to define a gap 2623 when delivery needle 2660 is slidably disposed within secondary lumen 2622. Gap 2623 may be configured to be loaded with a proximal delivery element of a tissue anchor. Gap 2623 may be configured to be loaded with a proximal delivery element such as a T-tag that is thin and elongate. Gap 2623 may be configured to be loaded with proximal delivery element such as a T-tag such as T-tag 1311 of tissue anchor 1300.

Combined delivery device 2600 may include a pushrod 2670. Pushrod 2670 may include a proximal portion 2670p and a distal portion 2670d. Pushrod 2670 may be slidably disposed within needle lumen 2661.

Pushrod 2670 may be configured to push a second retention element of a tissue anchor out of needle lumen 2661 of delivery needle 2660. Pushrod 2670 may be configured to push a first retention element of a tissue anchor out of needle lumen 2661.

Pushrod 2670 may include a channel 2679. Channel 2679 may be formed longitudinally at distal portion 2670d of pushrod 2670. Channel 2679 may be configured to allow a tension element of a tissue anchor to pass through. Channel 2679 may be aligned with slot 2669 of delivery needle 2660.

FIGS. 12A-12M show one embodiment of a method for delivering a gastrointestinal bypass device. Although delivery of gastrointestinal bypass device 1000 is shown as an example, the method may also be used to deliver other gastrointestinal bypass devices, such as gastrointestinal bypass devices 2000, 3000, and 4000.

Figure 12A:
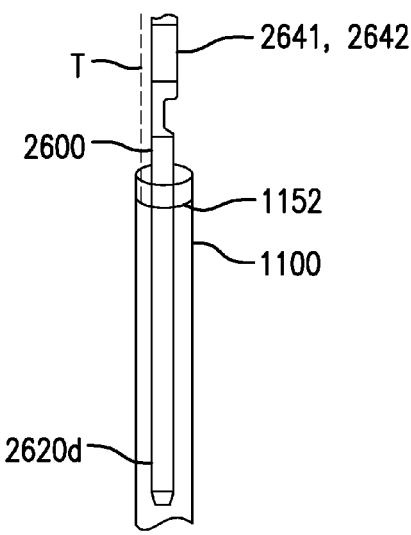
FIGS. 12A-12M show one embodiment of a method for delivering a gastrointestinal bypass device.

FIG. 12A shows loading cuff 1100 onto combined delivery device 2600. Distal portion 2620d of catheter 2620 may be inserted into the lumen of cuff 1100. Recess 2641 may be positioned inside drawstring 1152 of cuff 1100.

Figure 12B:
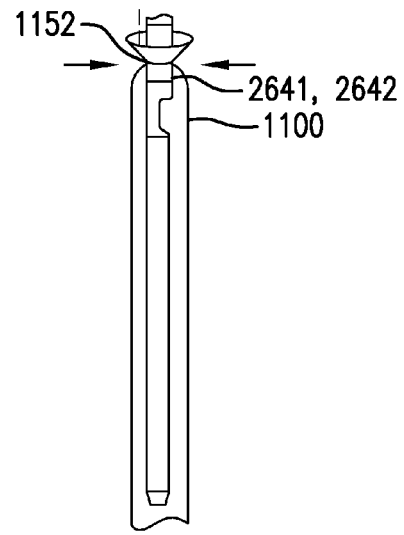

FIG. 12B shows forming a seal between combined delivery device 2600 and cuff 1100. Drawstring 1152 may be cinched into recess 2641 to form a seal between combined delivery device 2600 and cuff 1100. Drawstring 1152 may be cinched into sealing pad 2642.

Figure 12C:
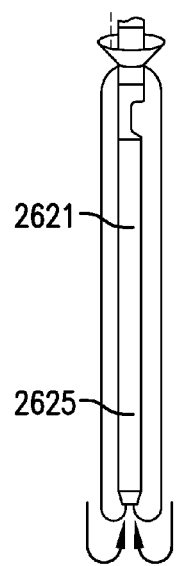

FIG. 12C shows inverting sleeve 1200 into primary lumen 2621 of catheter 2620. A loop snare may be inserted through proximal portion 2620*p* of catheter 2620 into primary lumen 2621. The loop snare may pass through sleeve 1200 and be coupled to distal portion 1250*d* of tube 1250. The loop snare may pull distal portion 1250*d* of tube 1250 into primary lumen 2621 to invert sleeve 1200 into primary lumen 2621.

Figure 12D:
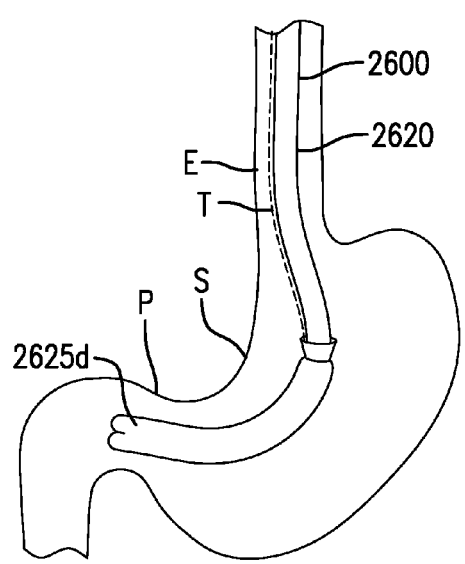

FIG. 12D shows positioning distal portion 2625*d* of sleeve delivery extension 2625 at or near the pylorus P. Catheter 2620 is advanced through the esophagus E and stomach S until distal portion 2625*p* of sleeve delivery extension 2625 is positioned at or near the pylorus P. An endoscope may be used in primary lumen 2621 to guide catheter 2620. A tether T may be used to adjust the position of cuff 1100 and/or control drawstring 1152.

Figure 12E:
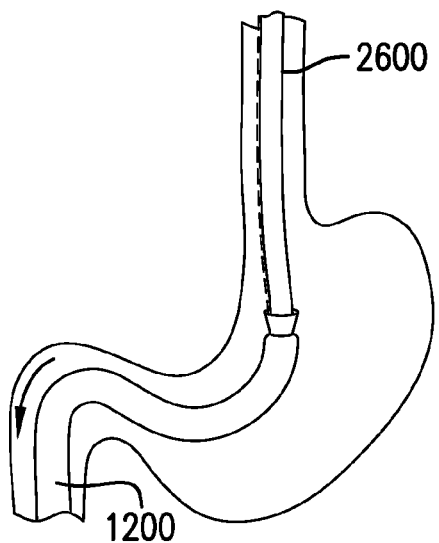

FIG. 12E shows everting sleeve 1200 into the intestine. The endoscope may be removed from primary lumen 2621 of catheter 2620. Distal portion 1250*d* of tube 1250 may be temporarily closed with a loop snare. Fluid may be pumped through primary lumen 2621 and/or secondary lumen 2622 to evert sleeve 1200 into the intestine. Distal portion 1250*d* of tube 1250 may then be opened.

Figure 12F:
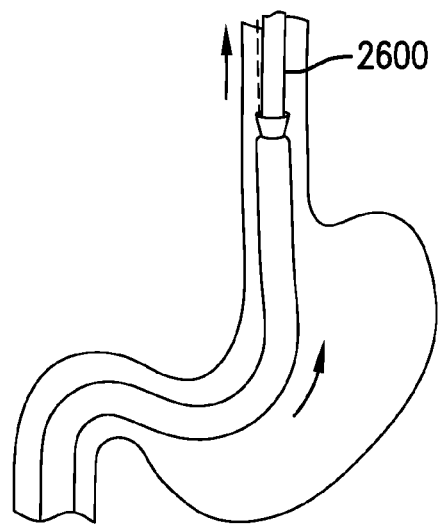

FIG. 12F shows positioning cuff 1100 at an attachment point. Catheter 2620 may be moved to position anchoring membrane 1131 of cuff 1100 at an attachment point in the esophagus E. Tissue marks made previously by tissue marking device 1400 may be used as a guide.

The attachment point may be approximately 5 mm to 25 mm above the opening of the stomach. The attachment point may be approximately 0 mm to 20 mm above the squamocolumnar junction (SCJ). The attachment point may be approximately 20 mm below to 50 mm above the diaphragm. The attachment point may be a proximal portion of the LES.

Figure 12G:
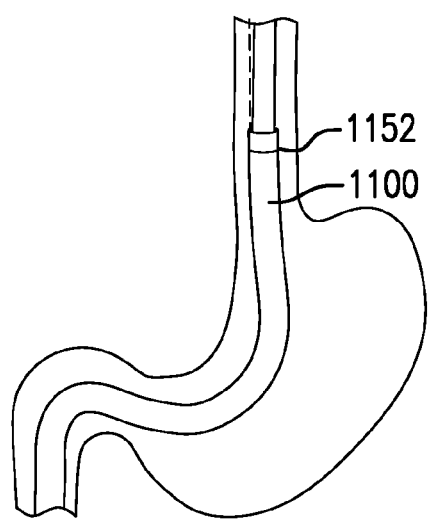

FIG. 12G shows releasing the seal between combined delivery device 2600 and cuff 1100. Drawstring 1152 may be uncinched to release the seal between combined delivery device 2600 and cuff 1100.

Distal portion 2620*d* of catheter 2620 is already in the lumen of cuff 1100. An endoscope may be used in primary lumen 2621 of catheter 2620 to guide catheter 2620 and visualize anchoring cavity 2630.

Figure 12H:
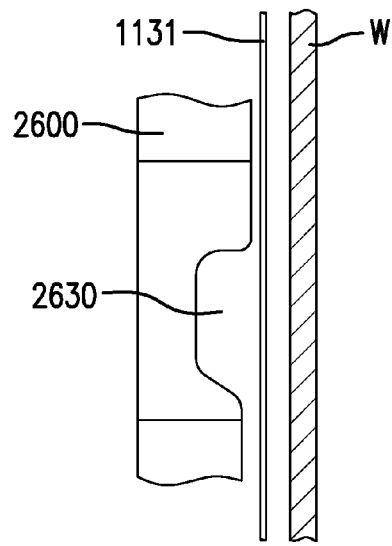

FIG. 12H shows positioning anchoring cavity 2630 of anchor delivery device 2600 next to anchoring membrane 1131 and the tissue wall W.

Figure 12I:
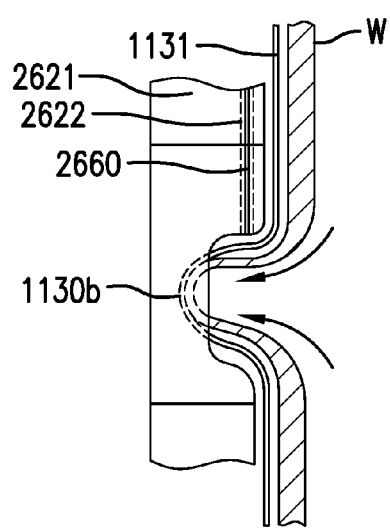

FIG. 12I shows forming a bulge 1130*b* in anchoring membrane 1131 and the tissue wall W. Delivery needle 2660 is retracted completely within secondary lumen 2622. A vacuum may be applied to anchoring cavity 2630 to draw anchoring membrane 1131 and the tissue wall W into anchoring cavity 2630 to form bulge 1130*b*. The vacuum may be approximately 50 mmHg to 500 mmHg.

Alternatively, anchoring membrane 1131 and the tissue wall W may be pulled into anchoring cavity 2630 by a grasper or other suitable device to form bulge 1130*b*. Alternatively, anchoring membrane 1131 and the tissue wall W may be allowed to enter anchoring cavity 2630 without assistance, such as from muscle activity of the tissue wall W, to form bulge 1130*b*.

Figure 12J:
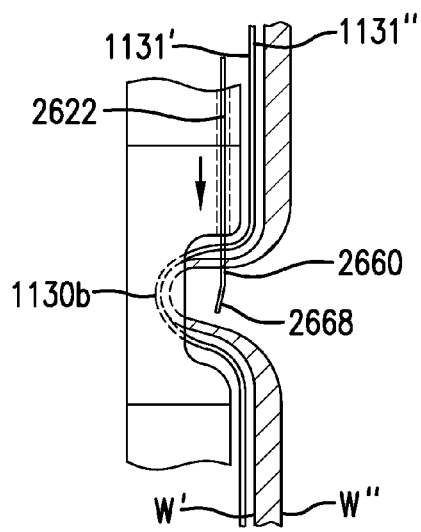

FIG. 12J shows piercing bulge 1130*b* from a first side 1131' of anchoring membrane 1131 and a first side W' of the tissue wall W. Delivery needle 2660 may be advanced a set distance out of secondary lumen 2622 of catheter 2620. Delivery needle 2660 may be advanced through bulge 1130*b* to position tip 2668 of delivery needle 2660 on a second side W" of the tissue wall W.

Delivery needle 2660 may be advanced in a direction substantially parallel to longitudinal axis 2620*a* of catheter. Delivery needle 2660 may be advanced in a direction substantially parallel to the tissue wall W other than bulge 1130*b*. Delivery needle 2660 may be advanced in a direction approximately 0 degrees to 10 degrees from parallel toward longitudinal axis 2620*a* of catheter. Delivery needle 2660 may be advanced in a direction approximately 0 degrees to 10 degrees from parallel away from the tissue wall W other than bulge 1130*b*.

Figure 12K:
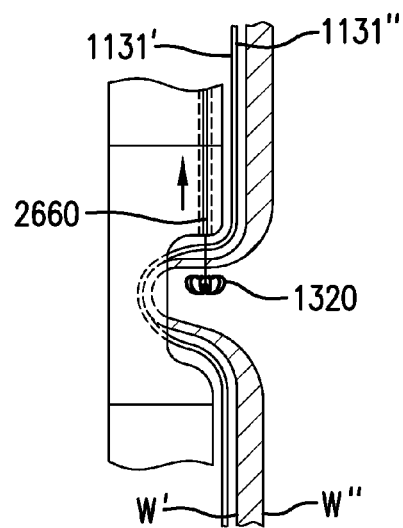

FIG. 12K shows placing second retention element 1320 of tissue anchor 1300 on a second side W" of the tissue wall W. Delivery needle 2660 may be pulled back over pushrod 2670 to release second retention element 1320 from needle lumen 2661. Alternatively, pushrod 2670 may be advanced a set distance through delivery needle 2660 to release second retention element 1320 from needle lumen 2661. A therapeutic agent may also be released from needle lumen 2661. Second retention element 1320 expands.

Figure 12L:
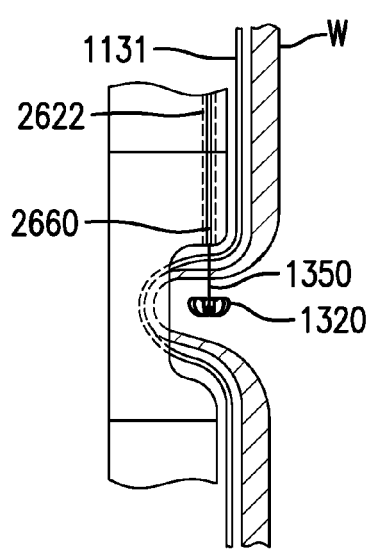

FIG. 12L shows placing tension element 1350 of tissue anchor 1300 through anchoring membrane 1131 and the tissue wall W. Delivery needle 2660 and pushrod 2670 may be pulled back through the tissue wall W and pulled back through anchoring membrane 1131 to place tension element 1350 through the tissue wall W and anchoring membrane 1131.

Delivery needle 2660 may be spring-loaded, so that any combination of the steps shown in FIGS. 12J-12L may be performed quickly, such as in 100 ms or less.

Figure 12M:
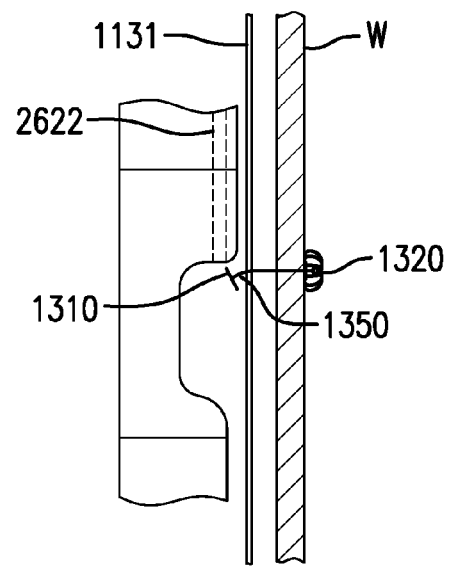

FIG. 12M shows placing first retention element 1310 of tissue anchor 1300 on first side 1131' of anchoring membrane 1131. Bulge 1130*b* may be released. Vacuum applied to anchoring cavity 2630 may be stopped. First retention element 1310 is placed on first side 1131' of anchoring membrane 1131. First retention element 1310 may be pulled out of secondary lumen 2622 of catheter 2620 by tension element 1350.

Alternatively, delivery needle 2660 may be advanced through bulge 1130*b* at both proximal side 2630*p* and distal side 2630*d* of anchoring cavity 2630, to position tip 2668 of delivery needle 2660 back on first side 1131' of anchoring membrane 1131. Second retention element 1320 may be placed on first side 1131' of anchoring membrane 1131, tension element 1350 may be placed through anchoring membrane 1131 and the tissue wall W at two points, and first retention element 1310 may also be placed on first side 1131' of anchoring membrane 1131.

Alternatively, delivery needle 2660 may be advanced only partially through bulge 1130*b* at proximal side 2630*p* of anchoring cavity 2630. Delivery needle 2660 may be advanced through anchoring membrane 1131 and only partially through the tissue wall W, to position tip 2668 of delivery needle 2660 within the tissue wall W, such as between layers of the tissue wall W. Second retention element 1320 may be placed within the tissue wall W, tension element 1350 may be placed through anchoring membrane 1131 and part of the thickness of tissue wall W, and first retention element 1310 may be placed on first side 1131' of anchoring membrane 1131.

Anchor delivery device 2600 may be rotated within cuff 1100 to deliver one or more additional tissue anchors. Delivery needle 2660 may be removed from secondary lumen 2622 to be reloaded with another tissue anchor, or exchanged for another delivery needle 2660 that has already been loaded.

While the foregoing has been with reference to particular embodiments of the invention, it will be appreciated by those skilled in the art that changes in these embodiments may be made without departing from the principles and spirit of the invention.

What is claimed is:

1. A delivery device for delivering a gastrointestinal bypass device, the gastrointestinal bypass device having a drawstring coupled at least partially around the gastrointestinal bypass device, the delivery device comprising:
 a catheter configured to be at least partially inserted into the gastrointestinal bypass device; and
 a sealing pad coupled around an outer surface of the catheter, the sealing pad configured to be cinched inside the drawstring to form a seal between the catheter and the gastrointestinal bypass device.

2. The delivery device of claim 1, further comprising:
 a recess formed around the catheter in the outer surface of the catheter.

3. The delivery device of claim 2, wherein the sealing pad is at least partially coupled in the recess.

4. The delivery device of claim 2, wherein a depth of the recess is substantially the same as a thickness of the sealing pad.

5. The delivery device of claim 1, further comprising:
 an anchoring cavity formed in the catheter, the anchoring cavity in communication with a primary lumen of the catheter.

6. The delivery device of claim 5, wherein the anchoring cavity is distal to the sealing pad.

7. The delivery device of claim 5, further comprising:
 a secondary lumen formed in the catheter, the secondary lumen having a distal portion positioned at a proximal side of the anchoring cavity.

8. The delivery device of claim 7, wherein the distal portion of the secondary lumen is angled from a longitudinal axis of the catheter at an angle of 0 degrees to 10 degrees.

9. The delivery device of claim 7, further comprising:
 a delivery needle slidably disposed in the secondary lumen, the delivery needle configured to be advanced out of and withdrawn into the secondary lumen.

10. The delivery device of claim 9, wherein the delivery needle includes a slot formed in a distal portion of the delivery needle.

11. The delivery device of claim 1, wherein the sealing pad includes a soft material.

12. The delivery device of claim 1, wherein the sealing pad includes silicone.

13. A delivery device for delivering a gastrointestinal bypass device, the gastrointestinal bypass device having a drawstring coupled at least partially around the gastrointestinal bypass device, the delivery device comprising:
 a catheter configured to be at least partially inserted into the gastrointestinal bypass device; and
 a sealing means around an outer surface of the catheter, the sealing means configured to be cinched inside the drawstring to form a seal between the catheter and the gastrointestinal bypass device.

* * * * *